US009526707B2

(12) United States Patent
Elford

(10) Patent No.: US 9,526,707 B2
(45) Date of Patent: Dec. 27, 2016

(54) METHODS FOR TREATING OR PREVENTING NEUROINFLAMMATION OR AUTOIMMUNE DISEASES

(76) Inventor: Howard L. Elford, Richmond, VA (US)

(*) Notice: Subject to any disclaimer, the term of this patent is extended or adjusted under 35 U.S.C. 154(b) by 375 days.

(21) Appl. No.: 12/228,440

(22) Filed: Aug. 13, 2008

(65) Prior Publication Data
US 2009/0047250 A1 Feb. 19, 2009

Related U.S. Application Data

(60) Provisional application No. 60/964,585, filed on Aug. 13, 2007.

(51) Int. Cl.
A61K 38/21 (2006.01)
A61K 31/33 (2006.01)
A61K 31/133 (2006.01)
A61K 31/15 (2006.01)
A61K 31/155 (2006.01)
A61K 31/16 (2006.01)
A61K 31/166 (2006.01)
A61K 31/17 (2006.01)
A61K 31/198 (2006.01)
A61K 31/27 (2006.01)
A61K 31/435 (2006.01)

(52) U.S. Cl.
CPC ............ A61K 31/133 (2013.01); A61K 31/15 (2013.01); A61K 31/155 (2013.01); A61K 31/16 (2013.01); A61K 31/166 (2013.01); A61K 31/17 (2013.01); A61K 31/198 (2013.01); A61K 31/27 (2013.01); A61K 31/435 (2013.01)

(58) Field of Classification Search
None
See application file for complete search history.

(56) References Cited

U.S. PATENT DOCUMENTS

| | | | |
|---|---|---|---|
| 2,848,430 A | 10/1954 | Frey et al. | |
| 3,629,443 A | 12/1971 | Lafon | |
| 4,253,322 A | 3/1981 | Vydrin et al. | |
| 4,263,322 A | 4/1981 | van't Riet et al. | |
| 4,394,389 A | 7/1983 | van't Riet et al. | |
| 4,448,730 A | 5/1984 | van't Riet et al. | |
| 4,623,659 A | 11/1986 | van't Riet et al. | |
| 4,814,432 A | 3/1989 | Freidinger et al. | |
| 4,837,304 A | 6/1989 | Garsky et al. | |
| 4,845,195 A | 7/1989 | Colonno et al. | |
| 4,942,253 A | 7/1990 | van't Riet et al. | |
| 5,071,835 A | 12/1991 | Guindon et al. | |
| 5,128,353 A | 7/1992 | Bergeron | |
| 5,135,917 A | 8/1992 | Burch | |
| 5,173,505 A | 12/1992 | Bergeron | |
| 5,183,828 A | 2/1993 | van't Riet et al. | |
| 5,198,425 A | 3/1993 | Rakhit et al. | |
| 5,292,775 A | 3/1994 | Bergeron | |
| 5,294,533 A | 3/1994 | Lupski et al. | |
| 5,350,770 A | 9/1994 | Elford et al. | |
| 5,366,996 A | 11/1994 | Elford et al. | |
| 5,391,563 A | 2/1995 | Bergeron | |
| 5,466,702 A | 11/1995 | Bergeron | |
| 5,476,841 A | 12/1995 | Deziel et al. | |
| 5,496,837 A | 3/1996 | Bergeron | |
| 5,496,838 A | 3/1996 | Bergeron | |
| 5,496,839 A | 3/1996 | Bergeron | |
| 5,496,840 A | 3/1996 | Bergeron | |
| 5,496,841 A | 3/1996 | Bergeron | |
| 5,498,622 A | 3/1996 | Bergeron | |
| 5,506,214 A * | 4/1996 | Beutler | 514/46 |
| 5,508,393 A | 4/1996 | McCarthy et al. | |
| 5,514,695 A | 5/1996 | Bergeron | |
| 5,519,041 A | 5/1996 | Bergeron | |
| 5,536,738 A | 7/1996 | Bergeron | |
| 5,536,739 A | 7/1996 | Bergeron | |
| 5,541,207 A | 7/1996 | Bergeron | |
| 5,545,649 A | 8/1996 | Bergeron | |
| 5,545,650 A | 8/1996 | Bergeron | |
| 5,550,144 A | 8/1996 | Bergeron | |
| 5,569,666 A | 10/1996 | Bergeron | |
| 5,589,587 A | 12/1996 | McCarthy et al. | |
| 5,627,158 A | 5/1997 | Cho-Chung | |
| 5,641,754 A | 6/1997 | Iversen | |
| 5,691,317 A | 11/1997 | Cho-Chung | |
| 5,760,210 A | 6/1998 | McCarthy et al. | |
| 5,767,134 A | 6/1998 | Li et al. | |
| 5,780,607 A | 7/1998 | Goodnow, Jr. et al. | |
| 5,786,138 A | 7/1998 | Swenson | |
| 5,849,903 A | 12/1998 | Pietrzkowski et al. | |

(Continued)

FOREIGN PATENT DOCUMENTS

DE 32 37 253 10/1983
DE 44 36 127 3/1996

(Continued)

OTHER PUBLICATIONS

Monica Rhodes, Yahoo Health (available online at http://heath.yahoo.com; accessed Jun. 1, 2010).*
Sumpter et al (Proc Amer Assoc Cancer Res 45:Abstract #2004, 2004).*
Beutler et al (Semin Hematol 33:45-52, 1996).*
Malecki et al (Drug Development Res 56:526-530, 2002).*
Merriam Webster Online Dictionary "prevent" definition (accessed online Jun. 1, 2010).*
Turchan et al (Neurology 60:307-314, 2003; Abstract only).*
Wallace (J Biomedicine and Biotechnol 2006:65741, Feb. 2006).*

(Continued)

Primary Examiner — Craig Ricci
(74) Attorney, Agent, or Firm — Ben Schroeder Law PL

(57) ABSTRACT

Disclosed herein are ribonucleotide reductase inhibitors, compositions comprising ribonucleotide reductase inhibitors, and methods for treating and/or preventing autoimmune diseases and neuroinflammatory diseases with the ribonucleotide reductase inhibitors.

6 Claims, 10 Drawing Sheets

(56) References Cited

U.S. PATENT DOCUMENTS

| | | | |
|---|---|---|---|
| 5,856,103 | A | 1/1999 | Gray et al. |
| 5,869,676 | A | 2/1999 | Niu et al. |
| 5,885,830 | A | 3/1999 | Saeki et al. |
| 5,919,772 | A | 7/1999 | Szyf et al. |
| 5,955,590 | A | 9/1999 | Levina et al. |
| 5,990,088 | A | 11/1999 | Ensoli et al. |
| 5,994,320 | A | 11/1999 | Low et al. |
| 5,998,383 | A | 12/1999 | Wright et al. |
| 5,998,602 | A | 12/1999 | Torrence et al. |
| 6,005,095 | A | 12/1999 | Capaccioli et al. |
| 6,007,995 | A | 12/1999 | Baker et al. |
| 6,013,522 | A | 1/2000 | Monia et al. |
| 6,017,898 | A | 1/2000 | Pietrzkowski et al. |
| 6,018,042 | A | 1/2000 | Mett et al. |
| 6,025,198 | A | 2/2000 | Bennett et al. |
| 6,030,942 | A | 2/2000 | Cooperman et al. |
| 6,033,910 | A | 3/2000 | Monia et al. |
| 6,040,296 | A | 3/2000 | Nyce |
| 6,046,004 | A | 4/2000 | Wu et al. |
| 6,046,319 | A | 4/2000 | Power et al. |
| 6,057,437 | A | 5/2000 | Kamiya et al. |
| 6,121,000 | A | 9/2000 | Wright et al. |
| 6,248,782 | B1 | 6/2001 | Elford et al. |
| 6,291,504 | B1 | 9/2001 | Nugiel et al. |
| 6,593,305 | B1 | 7/2003 | Wright |
| 6,924,308 | B1 | 8/2005 | Elford |
| 8,029,815 | B2 | 10/2011 | Elford et al. |
| 2003/0024534 | A1 | 2/2003 | Silvestri et al. |
| 2004/0126400 | A1 | 7/2004 | Iversen et al. |
| 2008/0050414 | A1 | 2/2008 | Elford et al. |
| 2009/0047250 | A1 | 2/2009 | Elford |
| 2012/0329870 | A1 | 12/2012 | Elford et al. |

FOREIGN PATENT DOCUMENTS

| | | |
|---|---|---|
| EP | 1 362 511 | 11/2003 |
| EP | 1 481 669 | 12/2004 |
| WO | WO 94/00135 | 1/1994 |
| WO | WO 98/20864 | 5/1998 |
| WO | WO 99/06009 | 2/1999 |
| WO | WO 99/30699 | 6/1999 |
| WO | WO 01/10454 | 2/2001 |
| WO | WO 01/49281 | 7/2001 |
| WO | WO 02/44321 | 6/2002 |
| WO | WO 02/055017 | 7/2002 |
| WO | WO 03/070188 | 8/2003 |
| WO | WO 03/103583 | 12/2003 |
| WO | WO 2004/006841 | 1/2004 |
| WO | WO 2004/080377 | 9/2004 |
| WO | WO 2005/027972 | 3/2005 |
| WO | WO 2005/115405 | 12/2005 |
| WO | WO 2005/123053 | 12/2005 |
| WO | WO 2006/128142 | 11/2006 |
| WO | WO 2007/104242 | 9/2007 |
| WO | WO 2007/128442 | 11/2007 |
| WO | WO 2008/021210 | 2/2008 |

OTHER PUBLICATIONS

Bowern et al (J Exp Med 160:1532-1543, 1984).*
Weigel et al (ASN Neuro 6:43-63, 2014).*
Theohardies (J Neuroinflammation 6:29-31, 2009).*
Rubens et al (Br J Cancer 64:1187-1188, 1991).*
Bardwell et al (Sleep Med Clin 3:61-71, 2008).*
www.mayoclinic.org (accessed online Feb. 29, 2016).*
The EP Search Report for EP08 25 2683 application dated Jun. 17, 2009.
Rubens et al. Phase II trial of didox in advanced breast cancer, Br. J. Cancer (1991), 64, 1187-1188.
Leustatin® (cladribine) Injection for Intravenous Infusion Only, Ortho Biotech Products, L.P., Raritan, NJ 08869, Aug. 2007.
Campbell et al. Didox therapy for demyelinating diseaseJournal of Neurochemistry, vol. 102, Aug. 6, 2007, p. 145.
Database CA, Chemical Abstracts Service, Columbus, Ohio, Nov. 8, 1965,Treatment of diabetesXP002531119, Database accession No. 1967:40714.
Vincent et al. Identification of candidate drugs for the treatment of ALS, Amyothrophic Lateral Sclerosis, London, GB, vol. 6, No. 1, Jan. 1, 2005, pp. 29-36.
Database WPI Week 199702, Treating Parkinsonian syndrome—by treatment with haloperidol at a dilution of 2:1000000, Thomson Scientific, London, GB; AN 1997-019281, XP002531120.
Fang et al. Hypoglycemic activity and chemical structure of the salicylates.Journal of Pharmaceutical Sciences, vol. 57, No. 12, Dec. 1968, pp. 2111-2116.
Wyss-Coray and Mucke, Inflammation in Neurodegenerative Disease—A Double-Edged Sword, 2002 Neuron, 35: 419-432.
Basu, Kraddy, and Levison, Interleukin-1: A Master Regulator of Neuroinflammation 2004 Journal of Neuroscience Research, 78(2): 151-156.
Griffin, Inflammation and neurodegenerative diseases2006 American Journal of Clinical Nutrition, 83(Suppl): 470S-474S.
Honig, Inflammation in Neurodegenerative Disease, 2000 Archives of Neurology, 57(6): 786-788.
Weydt and Moller, Neuroinflammation in the pathogenesis of amyotrophic lateral sclerosis2005 Neuroreport, 16(6):527-531.
Hunot and Hirsch, Neuroinflammatory Processes in Parkinson's Disease2003 Annals of Neurology, 53(Suppl 3): S49-S58.
McGeer and McGeer, Local neuroinflammation and the progression of Alzheimer's disease2002 Journal of Neurovirol., 8(6): 529-538.
Hull and Hampel, 9 Neuroinflammation in Alzheimer's Disease: Potential Targets for Disease-Modifying Drugs 2002 Ernst Schering Res Found Workshop, (39): 159-178.
Pardo, Vargas, and Zimmernlan, Immunity, neuroglia and neuroinflammation in autism, 2005 International Review of Psychiatry, 17(6): 485-495.
Godbout and Johnson, Age and Neuroinflammation: A Lifetime of Psychoneuroimmune Consequences 2006 Neurologic Clinics, 24(3): 521-538.
Rooker et al., Spatiotemporal Pattern of Neuroinflammation After Impact-Acceleration Closed Head Injury in the Rat2006 Mediators Inflammation, 2006(1): 90123.
Molcanyi et al., Trauma-Associated Inflammatory Response Impairs Embryonic Stem Cell Survival and Integration after Implantation into Injured Rat Brain 2007 Journal of Neurotrauma, 24(4): 625-637.
Tang et al., Regulatory T-cell physiology and application to treat autoimmunity2006 Immunol Rev. 212:217-237.
Dorner et al. The role of B cells in rheumatoid arthritis: mechanisms and therapeutic targets 2003 Curr. Opin. Rheumatol 15: 246-252.
Takemura et al. T Cell Activation in Rheumatoid Synovium Is B Cell Dependent 2001 J Immunol 107: 4710-4718.
Cua et al. Interleukin-23 rather than interleukin-12 is the critical cytokine for autoimmune inflammation of the brain 2003 Nature 421: 744-748.
Murphy et al. Divergent Pro- and Antiinflammatory Roles for IL-23 and IL-12 in Joint Autoimmune Inflammation 2003 J. Exp Med. 198: 1951-1957.
Langrish et al. IL-23 drives a pathogenic T cell population that induces autoimmune inflammation 2005 J. Exp Med. 201: 233-240.
Chen et al. Anti-IL-23 therapy inhibits multiple inflammatory pathways and ameliorates autoimmune encephalomyelitis 2006 J. Clin. Invest. 116: 1317-1326.
Park et al. A distinct lineage of CD4 T cells regulates tissue inflammation by producing interleukin 172005 Nat. Immunol. 6: 1133-1141.
Bettelli et al. Reciprocal developmental pathways for the generation of pathogenic effector $T_H17$ and regulatory T cells 2006 Nature 441: 235-238.
Steinman L. A brief history of $T_H17$, the first major revision in the $T_H1/T_H2$ hypothesis of T cell-mediated tissue damage 2007 Nature Med. 13, 139-145.
Furuzawa-Carballeda et al. Autoimmune inflammation from the Th17 perspective 2007 Autoimmun Rev; 6(3):169-175.

(56) References Cited

OTHER PUBLICATIONS

Young et al., Hydroxyurea-induced Inhibition of Deoxyribonucleotide Synthesis: Studies in Intact Cells Cancer Res. 27 (Part 1) pp. 526-534 (1967).
French et al., Journal of Medicinal Chemistry,α (N) Formylheteroaromatic Thiosemicarbazones. Inhibition of Tumor-Derived Ribonucleoside Diphosphate Reductase and Correlation with in Vivo Antitumor Activity 1974, vol. 17 (2), No. 2, p. 172.
Bolton, C.Recent advances in the pharmacological control of experimental allergic encephalomyelitis (EAE) and the implications for multiple sclerosis treatmentMult. Scler. 1995; 1(3); 143-9.
Kostulas et al. Increased IL-1{beta}, IL-8, and IL-17 mRNA Expression in Blood Mononuclear Cells Observed in a Prospective Ischemic Stroke Study 1999 Stroke 10:2174-2179.
Anderson HV et al. (1993) Restenosis after coronary angioplasty. J Intery Cardiol 6:187-202.
Bauters C and Isner JM (1997) the biology of restenosis. Prog Cardiovasc Dis 40:107-116.
Bennett MR and O'Sullivan M (2001) Mechanisms of angioplasty and stent restenosis: implications for design of rational therapy. Pharmacol Ther 91:149-166.
Bhargava B et al. (2003) New approaches to preventing restenosis. BMJ 327:274-279.
Crook MF and Akyurek LM (2003) Gene transfer strategies to inhibit neointima formation. Trends Cardiovasc Med 13:102-106.
Drachman DE et al., (2000) Neointimal thickening after stent delivery of paclitaxel: change in composition and arrest of growth over six months. J Am Coll Cardiol 36:2325-2332.
Duilio C et al., (2001) Neutrophils are primary source of 02 radicals during reperfusion after prolonged myocardial ischemia. Am J Physiol Heart Circ Physiol 280:H2649-2657.
Elezi S et al. (1998) Vessel size and long-term outcome after coronary stent placement. Circulation 98:1875-1880.
Elford HL (1968) Effect of hydroxyurea on ribonucleotide reductase. Biochem Biophys Res Commun 33:129-135.
Elford HL et al. (1970) Ribonucleotide reductase and cell proliferation. I. Variations of ribonucleotide reductase activity with tumor growth rate in a series of rat hepatomas. J Biol Chem 245:5228-5233.
Elford HL, Wampler GL and van't Riet B (1979) New ribonucleotide reductase inhibitors with antineoplastic activity. Cancer Res 39:844-851.
Epstein SE et al. (1991) Cytotoxic effects of a recombinant chimeric toxin on rapidly proliferating vascular smooth muscle cells. Circulation 84:778-787.
Farb A et al. (2002) Morphological predictors of restenosis after coronary stenting in humans. Circulation 105:2974-2980.
Fischman DL et al. (1994) A randomized comparison of coronary-stent placement and balloon angioplasty in the treatment of coronary artery disease. Stent Restenosis Study Investigators. N Engl J Med 331:496-501.
Fritzer-Szekeres et al. (2000) Trimidox, an inhibitor of ribonucleotide reductase, induces apoptosis and activates caspases in HL-60 promyelocytic leukemia cells. Exp Hematol 28:924-930.
Fritzer-Szekeres et al. (1997) Iron binding capacity of didox (3,4-dihydroxybenzohydroxarnie acid) and amidox (3,4-dihydroxybenzamidoxime) new inhibitors of the enzyme ribonucleotide reductase. Life Sci 61:2231-2237.
Fritzer-Szekeres M et al. (2002) Trimidox, an inhibitor of ribonucleotide reductase, synergistically enhances the inhibition of colony formation by Ara-C in HL-60 human promyelocytic leukemia cells. Biochem Pharmacol 64:481-485.
Gershlick A et al. (2004) Inhibition of restenosis with a paclitaxel-eluting, polymer-free coronary stent: the European Evaluation of Paclitaxel Eluting Stent (ELUTES) trial. Circulation 109:487-493. Epub Jan. 2004 2026.
Goldschmidt-Clermont PJ and Moldovan L (1999) Stress, superoxide, and signal transduction. Gene Expr 7, 255-260.
Grube E et al. (2003) TAXUS 1: six- and twelve-month results from a randomized, double-blind trial on a slow-release paclitaxel-eluting stent for de novo coronary lesions. Circulation 107:38-42.
Gupta C and Yaffe SJ (1982) Phenobarbital-induced alterations in the sexual differentiation of the female rat: reversal by hydroxyurea and cycloheximide Pediatr Pharmacol (New York) 2:85-91.
Heckenkamp J, Gawenda M and. Brunkwall J (2002) Vascular restenosis. Basic science and clinical implications. J Cardiovasc Surg (Torino) 43:349-357.
Heldman AW et al. (2001) Paclitaxel stent coating inhibits neointimal hyperplasia at 4 weeks in a porcine model of coronary restenosis. Circulation 103:2289-2295.
Horvath Z et al. (2004) Synergistic cytotoxicity of the ribonucleotide reductase inhibitor didox (3,4-dihydroxybenzohydroxamic acid) and the alkylating agent carmustine (BCNU) in 9L rat gliosarcoma cells and DAOY human medulloblastoma cells. Cancer Chemother Pharmacol. 54(2):139-45.
Inayat MS et al. (2002) Didox (a novel ribonucleotide reductase inhibitor) overcomes Bcl-2 mediated radiation resistance in prostate cancer cell line PC-3. Cancer Biol Ther 1:539-545.
Indolfi C et al. (2003) Molecular mechanisms of in-stent restenosis and approach to therapy with eluting stents. Trends Cardiovasc Med 13:142-148.
Kastrati A et al. (2005) Sirolimus-eluting stent or paclitaxel-eluting stent vs balloon angioplasty for prevention of recurrences in patients with coronary in-stent restenosis: a randomized controlled trial. Jama 293:165-171.
Kim JW et al. (2005) Delayed severe multivessel spasm and aborted sudden death after Taxus stent implantation. Heart 91:e15.
Lanza GM et al. (2002) Targeted antiproliferative drug delivery to vascular smooth muscle cells with a magnetic resonance imaging nanoparticle contrast agent: implications for rational therapy of restenosis. Circulation 106:2842-2847.
Lee R et al. (1997) Selective inhibition of 1κBα phosphorylation and HIV-1 LTR-directed gene expression by novel antioxidant compounds. Virology 234:277-290.
Libby P and Tanaka H (1997) The molecular bases of restenosis. Prog Cardiovasc Dis 40:97-106.
Mayhew CN et al. (2002) Short-term treatment with novel ribonucleotide reductase inhibitors Trimidox and Didox reverses late-stage murine retrovirus-induced lymphoproliferative disease with less bone marrow toxicity than hydroxyurea. Antivir Chem Chemother 13:305-314.
Mayhew CN et al. (1999) In vivo and in vitro comparison of the short-tern hematopoietic toxicity between hydroxyurea and trimidox or didox, novel ribonucleotide reductase inhibitors with potential anti-HIV-1 activity. Stem Cells 17:345-356.
Sirolimus- vs Paclitaxel-Eluting Stents in De Novo Coronary Artery Lesions the Reality Trial: A Randomized Controlled Trial, JAMA, Feb. 2006, vol. 295, No. 8, 895-904.
Natsumeda Y (1985) Purine enzymology of human colon carcinomas. Cancer Res 45:2556-2559.
Noda-Heiny H and Sobel BE (1995) Vascular smooth muscle cell migration mediated by thrombin and urokinase receptor. Am J Physiol 268:C1195-1201.
Pacelli R et al. (1996) Hydroxyurea reacts with heme proteins to generate nitric oxide. Lancet 347:900.
Sarkar R et al. (1997) Cell cycle effects of nitric oxide on vascular smooth muscle cells. Am J Physiol 272:H1810-1818.
Sarkar R and Webb RC (1998) Does nitric oxide regulate smooth muscle cell proliferation? A critical appraisal. J Vasc Res 35:135-142.
Segev A et al. (2002) Inhibition of vascular smooth muscle cell proliferation by a novel fibroblast growth factor receptor antagonist. Cardiovasc Res 53:232-241.
Shet AS et al. (2003) Sickle blood contains tissue factor-positive microparticles derived from endothelial cells and monocytes. Blood 102:2678-2683.
Sousa JE et al. (2001) Lack of neointimal proliferation after implantation of sirolimus-coated stents in human coronary arteries: a quantitative coronary angiography and three-dimensional intravascular ultrasound study. Circulation 103:192-195.

(56) References Cited

OTHER PUBLICATIONS

Stolze K and Nohl H (1990) EPR studies on the oxidation of hydroxyurea to paramagnetic compounds by oxyhemoglobin. Biochem Pharmacol 40:799-802.
Stone GW et al. (2004) One-year clinical results with the slow-release, polymer-based, paclitaxel-eluting TAXUS stent: the TAXUS-IV trial. Circulation 109:1942-1947.
Suzuki T et al. (2001) Stent-based delivery of sirolimus reduces neointimal formation in a porcine coronary model. Circulation 104:1188-1193.
Takeda E and Weber G (1981) Role of ribonucleotide reductase in expression in the neoplastic program. Life Sci 28:1007-1014.
Tanaka H et al. (2000) A ribonucleotide reductase gene involved in a p53-dependent cell-cycle checkpoint for DNA damage. Nature 404:42-49.
Turchan J et al. (2003) Oxidative stress in HIV demented patients and protection ex vivo with novel antioxidants. Neurology 60:307-314.
Ueda M et al. (1995) Smooth muscle cell de-differentiation is a fundamental change preceding wound healing after percutaneous transluminal coronary angioplasty in humans. Coron Artery Dis 6:71-81.
Vaughan WP, Holm C and Cordel K (1989) Hydroxyurea potentiation of the antineoplastic activity of cyclophosphamide and 4'-(9-acridinylamino)methanesulfon-M-anisidide (AMSA) in the brown Norway rat myelocytic leukemia model. Cancer Chemother Pharmacol 23:26-30.
Ward MR et al. (2000) Arterial remodeling. Mechanisms and clinical implications. Circulation 102:1186-1191.
Letsinger et al. Cholesteryl-conjugated oligonucleotides: Synthesis, properties, and activity as inhibitors of replication of human immunodeficiency virus in cell culture. Proc Natl Acad Sci USA (1989) 86:6553-6556.
Gitlin et al. Short interfering RNA confers intracellular antiviral immunity in human cells (2002) Nature 418:430-4.
Caplen et al. Specific inhibition of gene expression by small double-stranded RNAs in invertebrate and vertebrate systems (2001) Proc. Natl. Acad. Sci. 98:9742-9747.
Elbashir et al. Duplexes of 21-nucleotide RNAs mediate RNA interference in cultured mammalian cells (2001) Nature 411:494-8.
Duxbury et al., RNA interference targeting the M2 subunit of ribonucleotide reductase enhances pancreatic adenocarcinoma chemosensitivity to gemcitabine(2004) Oncogene. 23(8):1539-1548.
Duxbury et al. Retrovirally mediated RNA interference targeting the M2 subunit of ribonucleotide reductase: A novel therapeutic strategy in pancreatic cancer (2004) Surgery. 136(2):261-269.
Lin et al. Stable Suppression of the R2 Subunit of Ribonucleotide Reductase by R2-targeted Short Interference RNA Sensitizes p53(_/_) HCT-116 Colon Cancer Cells to DNA-damaging Agents and Ribonucleotide Reductase Inhibitors (2004) Biol. Chem., 279(26):27030-27038.
Senter et al. Generation of 5-Fluorouracil from 5-Fluorocytosine by Monoclonal Antibody-Cytosine Deaminase Conjugates (1991) Bioconjugate Chem., 2:447-451.
Bagshawe, Towards generating cytotoxic agents at cancer sites (1989) Br. J. 15 Cancer, 60:275-281.
Bagshawe et al., A cytotoxic agent can be generated selectively at cancer sites (1988) Br. J. Cancer, 58:700-703.
Senter et al , Generation of Cytotoxic Agents by Targeted Enzymes (1993) Bioconjugate Chem., 4:3-9.
Battelli et al., T lymphocyte killing by a xanthine-oxidase-containing immunotoxin (1992) Cancer Immunol. Immunother. 35:421-425.
Pietersz et al. Antibody Conjugates for the Treatment of Cancer(1992) Immunolog. Reviews, 129:57-80.
Roffler et al., Anti-neoplastic glucuronide prodrug treatment of human tumor cells targeted with a monoclonal antibody-enzyme conjugate (1991) Biochem. Pharmacol., 42:2062-2065.

Brown et al.,Molecular and Cellular Mechanisms of Receptor-Mediated Endocytosis (1991) DNA and Cell Biology 10:6, 399-409.
Pastan et al.,a retrovirus carrying an MDRJ cDNA confers multidrug resistance and polarized expression of P-glycoprotein in MDCK cells (1988) Proc. Natl. Acad. Sci. U.S.A. 85:4486.
Miller et al., Redesign of Retrovirus Packaging Cell Lines to Avoid Recombination Leading to Helper Virus Production (1986) Mol. Cell. Biol.6:2895.
Mitani et al. Transduction of Human Bone Marrow by Adenoviral Vector (1994) Hum. Gene Ther. 5:941-948).
Goodman et al. Recombinant adeno-associated virus-mediated gene transfer into hematopoietic progenitor cells 25 (1994) Blood 84:1492-1500.
Naldini et al., In Vivo Gene Delivery and Stable Transduction of Nondividing Cells by a Lentiviral Vector (1996) Science 272:263267.
Agrawal et al. Cell-cycle kinetics and YSY-G pseudotyped retrovirus-mediated gene transfer in blood-derived $CD34^+$ cells (1996) Exper. Hematol. 24:738747.
Schwartzenberger et al. Targeted gene transfer to human hematopoietic progenitor cell lines through the c-kit receptor (1996) Blood 87:472-478.
Greenland et al. Commentary: Lifelong prevention of atherosclerosis: the critical importance of major risk factor exposures International J. of Epidemiology 2002; 31: 1129-1134.
Sidney Blumenthal, Prevention of Atherosclerosis, The American Journal of Cardiology; vol. 31, Issue 5, May 1973, pp. 591-594.
Merriam Webster Dictionary entries for the terms:"prevent" and "restenosis" (2 entries).
Brune Wolfram et al. A ribonucleotide reductase homolog of cytomegalovirus and endothelial cell tropism, Science, 2001, v. 291:5502, p. 303.
Henry J C et al. Inhibition of Ribonucleotide Reductase Reduces Neoiptimal Formation Following Balloon Injury, Journal of Pharmacology and Experimental Therapeutics, American Society for Pharmacology and Experimental Therapeutics, US, vol. 314, No. 1, p. 70, Feb. 2005.
Yamauchi et al. Current systemic therapies for psoriasis: Where are we now? J. Am. Acad. Dermatol. (2003) vol. 49, No. 2, pp. S66-S77.
International Preliminary Report on Patentability for PCT/US05/014581, filed Apr. 27, 2005.
Dhananjay Kaul et al. Robust Vascular Protective Effect of Hydroxamic Acid Derivatives in a Sickle Mouse Model of Inflammation, Microcirculation, 13: 1-9, 2006.
Carmichael et al. A phase and I pharmacokinetic study of didox administered by 36 hour infusion, Br. J. Cancer, 61, 447-450, 1990.
Veale et al. A phase 1 and pharmacokinetic study of didox: A ribonucleotide reductase inhibitor, Br. J. Cancer, 58, 1988.
Warnke et al. Identification of targets and new developments in the treatment of multiple sclerosis—focus on cladribine, Drug Design, Development and Therapy, 4, 117-126, 2010.
Griffig et al. Mechanisms of Inhibition of DNA Synthesis by 2-Chlorodeoxyadenosine in Human Lymphoblastic Cells, Cancer Research, 49, 6923-6928, 1989.
Carrera et al.. Potent Toxicity of 2-Chlorodeoxyadenosine toward Human Monocytes in Vitro and In Vivo, The American Society for Clinical Investigation, Inc., vol. 86, 1480-1488, 1990.
Carlson, N. et al., "Antioxidants in Multiple Sclerosis: Do They Have a Role in Therapy?" 2006, CNS Drugs, 20(6): 433-441.
Elford, H. and Van't Riet, B., "The Inhibition of Nucleoside Diphosphate Reductase by Hydroxybenzohhydroxamic Acid Derivatives," In: International Encyclopedia of Pharmacology and Therapeutics (eds. Cory, J.G. and Cory, A.H.), 1989, pp. 217-233.
Graslund, A. et al., "Characterization of the Free Radical of Mammalian Ribonucleotide Reductase," 1982, J. Biol. Chem., 257(10): 5711-5715.
Kjöller-Larsen, I. et al., "Characterization of the Active Site of Ribonucleotide Reductase of *Escherichia coli*, Bacteriophage T4 and Mammalian Cells by Inhibition Studies with Hydroxyurea Analogues," 1982, Eur. J. Biochem., 125: 75-81.
Miller, M.J., "Syntheses and Therapeutic Potential of Hydroxamic Acid Based Siderophores and Analogues," Chem. Rev., 89(7): 1563-1579.

(56) References Cited

OTHER PUBLICATIONS

Verbeek, R. et al., "Oral Flavonoids Delay Recovery from Experimental Autoimmune Encephalomyelitis in SJL Mice," 2005, Biochem. Pharma., 20: 220-228.
Chen, T.-H. et al., "Randomized, double-blind, placebo-controlled trial of hydroxyurea in spinal muscular atrophy," 2010, Neurology 75:2190-2197.
Go, V. et al., "Paradoxical response to prophylactic Didox (N-3, 4 trihydroxybenzamide) treatment in murine cytomegalovirus-infected mice," 2011, Antiviral Therapy 16:1277-1286.
Grzeschik, S. et al., "Hydroxyurea Enhances SMN2 Gene Expression in Spinal Muscular Atrophy Cells," 2005, Ann. Neurol. 58:194-202.
Horvath, Z. et al., "Synergistic cytotoxicity of the ribonucleotide reductase inhibitor didox (3,4-dihydroxy-benzohydroxamic acid) and the alkylating agent carmustine (BCNU) in 9L rat gliosarcoma cells and DAOY human medulloblastoma cells," 2004, Cancer Chemother. Pharmacol. 54:139-145.
Inayat, M. et al., "Inhibition of allogeneic inflammatory responses by the Ribonucleotide Reductase Inhibitors, Didox and Trimidox," 2010, J. Inflammation 7:43 (pp. 1-11).
Iyamu, W. et al., "Enhancement of Hemoglobin and F-Cell Production by Targeting Growth Inhibition and Differentiation of K562 Cells with Ribonucleotide Reductase Inhibitors (Didox and Trimidox) in Combination with Streptozotocin," 2000, Am. J. Hematol. 63(4):176-183.
Liang, W. et al., "The effect of hydroxyurea in spinal muscular atrophy cells and patients," 2008, J. Neurolog. Sci. 268:87-94.
Mayhew, C. et al., "Effective Use of Ribonucleotide Reductase Inhibitors (Didox and Trimidox) Alone or in Combination with Didanosine (ddI) to Suppress Disease Progression and Increase Survival in Murine Acquired Immunodeficiency Syndrome (MAIDS)," 1997, Cell. Mol. Biol. 43(7):1019-1029.
Mayhew, C. et al., "In vivo and in vitro comparison of the short-term hematopoietic toxicity between hydroxyurea and trimidox or didox, novel ribonucleotide reductase inhibitors with potential anti-HIV-1 activity," 1999, Stem Cells 17(6):345-356.
Mayhew, C. et al., "Short-term treatment with novel ribonucleotide reductase inhibitors Trimidox and Didox reverses late-stage murine retrovirus-induced lymphoproliferative disease with less bone marrow toxicity than hydroxyurea," 2002, Antiviral Chem. Chemother., 13(5):305-314.
Mayhew, C. et al., "Suppression of retrovirus-induced immunodeficiency disease (murine AIDS) by trimidox and didox Novel ribonucleotide reductase inhibitors with less bone marrow toxicity than hydroxyurea," 2002, Antiviral Res. 56:167-181.
Mayhew, C. et al., "Combination of inhibitors of lymphocyte activation (hydroxyurea, trimidox, didox) and reverse transcriptase (didanosine) suppresses development of murine retrovirus-induced lymphoproliferative disease," 2005, Antiviral Res. 65:13-22.
Minagar, A. et al., "The role of macrophage/microglia and astrocytes in the pathogenesis of three neurologic disorders: HIV-associated dementia, Alzheimer disease, and multiple sclerosis," 2002, J. Neurol. Sci. 202:13-23.
Pace, B. et al., "Transgenic Mouse Model of Pharmacologic Induction of Fetal Hemoglobin: Studies Using a New Ribonucleotide Reductase Inhibitor, Didox," 1994, Am. J. Hematol. 45:136-141.
Turchan, J. et al., "Oxidative stress in HIV demented patients and protection ex vivo with novel antioxidants," 2003, Neurology 60:307-314.
Xu, C. et al., "Hydroxyurea enhances SMN2 gene expression through nitric oxide release," 2011, Neurogenetics 12:19-24.
Morsali et al. (Abstract), "Safinamide and flecainide protect axons and reduce microglial activation in models of multiple sclerosis", Brain, 2013, 136(Pt 4) 1067.
Stankiewicz et al., "Iron and multiple sclerosis", Neurobiology of Aging, 35, (2014), S51-S58.
Fiebiger et al., "The antioxidant idebenone fails to prevent or attenuate chronic experimental autoimmune encephalomyelitis in the mouse", Journal of Neuroimmunology, 262, (2013), pp. 66-71.
Elford et al. The Inhibition of Necleoside Diphosphate Reactase by Hydroxybenzohydroxamic Acid Derivatives, Chapter 11, Oxford, United Kingdom Pergamon Press;1989, pp. 217-233.
Szekeres et al., Eur J. Clin Chem Clin Biochem. Nov. 1995;33(11):785-789.
Kanno et al., Biol.Pharm. Bull. 30(5), 994-998 (2007).
Rauko P. et al., Anticancer Res. Sep.-Oct. 1997;17(5A):3437-40).

* cited by examiner

METHODS FOR TREATING OR PREVENTING NEUROINFLAMMATION OR AUTOIMMUNE DISEASES

CROSS REFERENCE TO RELATED APPLICATIONS

This application claims the benefit of priority to U.S. Provisional Application No. 60/964,585, filed on Aug. 13, 2007, which is incorporated by reference herein in its entirety.

FIELD OF THE INVENTION

Disclosed herein are ribonucleotide reductase inhibitors that can be used to treat one or more autoimmune diseases and neuroinflammatory diseases, inter alia, multiple sclerosis.

BACKGROUND

Neuroinflammation is an important constituent of many neurodegenerative diseases. In most of these diseases, neurons become stressed as a result of a toxic accumulation of substances, as in the case of sphingolipidoses (e.g. Tay-sachs Disease, Krabbe's Disease, Gaucher's Disease, Farber's Disease, Sandhoff's Disease, Niemann-Pick Disease, Fabry's Disease). The stressed neuron can then activate astrocytes or astroglia to produce inflammatory cytokines. These inflammatory cytokines, in turn, have further deleterious effects on neurons in the vicinity. The activated astrocytes and microglia can attract lymphocytes, further exacerbating the entire process (Wyss-Coray and Mucke, 2002 *Neuron*, 35: 419-432.)

One of the key inflammatory cytokines is interleukin-1, which is known to be a key pro-inflammatory cytokine over-expressed by activated microglia (Basu, Kraddy, and Levison, 2004 *Journal of Neuroscience Research*, 78(2): 151-156.). This cytokine can cause death of neurons, which will activate more microglia, and in turn more interleukin-1 will be produced so that the production of this pro-inflammatory cytokine is a self-sustaining and self-amplifying system (Griffin, 2006 *American Journal of Clinical Nutrition*, 83(Suppl): 470S-474S.). It has been known for some time that inflammatory cytokines are elevated in Alzheimer's and Parkinson's patients and are postulated to be major contributors to the pathogenesis of these neurological disorders (Perlmutter, 2000 *Archives of Neurology*, 57(6): 786-788.). Another neurological disease with a key neuroinflammatory component is amyotrophic lateral sclerosis in which motor neurons die. Recent evidence suggests that neuroinflammation and microglial cells play a key role in this neuroinflammatory disorder and in animal models of this disease (Weydt and Moller, 2005 *Neuroreport*, 16(6):527-531.). Parkinson's disease is another neurodegenerative disease with a key neuroinflammatory component. Brains taken from Parkinson's patients show a very conspicuous glial cell neuroinflammatory reaction, which is manifested by elevated cytokine levels and up-regulation of inflammatory-associated factors, such as cyclo-oxygenase-2 and inducible nitric-oxide synthase (Hunot and Hirsch, 2003 *Annals of Neurology*, 53(Suppl3): S49-S58.).

Alzheimer's disease is another important neurodegenerative condition in which chronic inflammation is very closely linked to lesioned areas of the brain. Activated microglial, cytokines, and chemokines are associated with this disease. Inflammatory mediators are locally produced and elevated in the affected regions of Alzheimer's brains (McGeer and McGeer, 2002 *Journal of Neurovirol.*, 8(6): 529-538.). Many authors have suggested that neuroinflammation is a potential target for modifying the course of Alzheimer's disease (Hull and Hampel, 2002 *Ernst Schering Res Found Workshop*, (39): 159-178.).

Another important neurodegenerative disease in which neuroinflammation plays a key role is multiple sclerosis. Inflammatory mediators and activated microglial are also found in the demyelinated areas of the brain.

As mentioned previously, there are a number of other neurological diseases in which products accumulate abnormally in neurons and cause abnormal stress. In turn, the stress of the neuron can activate microglial and astrocytes, and produce an inflammatory response. These diseases include Hurler's Syndrome, Scheie's Syndrome, Hunter's Syndrome, San Fillipo's Syndrome, Maroteaux-Lany Syndrome, Sly Syndrome, Fucosidosis, Alpha-mannosidosis, Beta-mannosidosis, Schindler's Disease, Pompeii's Disease, Woman's Disease, and Infantile Neuronal Ceroid Lipofuscinosis.

Another neurodegenerative disease in which neuroinflammation is thought to play a role is autism. Recent evidence suggests that there is neuroglial activation in brain tissue and cerebrospinal fluid in patients with autism, indicating an important role for neural inflammation in autism (Pardo, Vargas, and Zimmerman, 2005 *International Review of Psychiatry*, 17(6): 485-495.). Other investigators have suggested that neuroinflammation increases with aging, and that this exacerbated neural inflammation can impair neuronal plasticity and lead to a heightened neuroinflammatory response in aged individuals (Godbout and Johnson, 2006 *Neurologic Clinics*, 24(3): 521-538.).

Finally, traumatic brain injury (TBI) is a neurodegenerative disease of importance in which neuroinflammation is a major contributor to the neuro-destructive process. Investigators have suggested that inflammation after TBI may be involved in tissue damage in sites other than the localized injury (Rooker et al., 2006 *Mediators Inflammation*, 2006 (1): 90123). Another interesting aspect of neuroinflammation in the CNS is the recent report that the trauma-associate inflammatory response may impair embryonic stem cell survival and integration after injury (Molcanyi et al., 2007 *Journal of Neurotrauma*, 24(4): 625-637.). Clearly, neuroinflammation is a key component of many neurodegenerative diseases and control of this process may prevent tissue damage and promote recovery.

Autoimmune disorders are characterized by the body producing an inappropriate immune response against its own tissue. At times the immune system will cease to recognize one or more of the body's normal constituents as self and create autoantibodies that attach to its own cells, tissues and/or organs. This induces inflammation and injury and leads to autoimmune disease.

The immune system is the body's method of protection against microorganisms and other foreign substances. It is composed of two key components as well as others. One component, B-lymphocytes, specialized white blood cells, produces antibodies, proteins that attached to foreign substances and rid them from the body. The other component consists of special white blood cells called T lymphocytes, which attack foreign substances directly. The largest group of autoimmune diseases consists of T-cell-mediated autoimmune disorders including type I diabetes, rheumatoid arthritis, psoriasis, inflammatory bowel disease, and multiple sclerosis (Tang et al. 2006 *Immunol Rev.* 212: 217-237). This is only a partial list, since some scientists have classified more than eighty disorders as autoimmune diseases. In these diseases, T cells, which express CD4 and CD8 surface proteins respectively, generate cytokines and cytolytic granules that directly destroy the targeted tissues. There are multiple pathways to tissue destruction. For example, the CD8+ T cells can interact directly with a target cell, such as an islet or a neuron and lyse the cell. In addition, cytokines, including TNFα also destroy tissues by triggering a suicide event, apoptosis, with the target cell. T-cells come in a number of subtypes. Since T-cells play such an important role in a number of autoimmune diseases, the regulation of T-cell activity has become an attractive therapeutic target. The products of T-cell activation, the inflammatory cytokines and chemokines such as TNF-α, IL-1, IL-6, IL-10, IL-12 and IL-17, are indicative that the regulation of these cytokines' expression will have a beneficial effect.

An expanding body of research data reveals a connection between B cells and rheumatoid arthritis and other autoimmune disorders (Dorner et al. 2003 *Curr. Opin. Rheumatol* 15: 246-252). Also the interaction of B cells and T-cells plays an important role in the pathogenesis of rheumatoid arthritis and other autoimmune disorders (Takemura et al. 2001 *J. Immunol* 107: 4710-4718). B cells produce proinflammatory cytokines such as TNFα, IL-1 and IL-6. The role of IL-6 with regard to autoimmunity has gained more importance with the recognition that IL-6 induces differentiation of B cells to antibody producing plasma cells, induces activated T cells, acts on hepatocytes to induce acute-phase reactants, including C-reactive protein (CRP) and fibrinogen, and decreases serum albumin levels.

Until recently, it was believed that there were only two types of T helper cells: $T_H1$ and $T_H2$. Considerable new evidence indicates that a new type of cells called $T_H17$ helper cells may play an important role in the pathogenesis of autoimmune disease (Cua et al. 2003 *Nature* 421: 744-748, Murphy et al. 2003 *J. Exp Med.* 198: 1951-1957, Langrish et al. 2005 *J. Exp Med.* 201: 233-240, Chen et al. 2006 *J. Clin. Invest.* 116: 1317-1326). The $T_H17$ helper cells produce a cytokine called IL-17, thought to cause late occurring inflammation by recruiting immune cells to peripheral tissues (Park et al. 2005 *Nat. Immunol.* 6: 1133-1141). Many lines of evidence indicate that IL-17 is a pathogenic effecter molecule in autoimmunity. IL-6 promotes the development of T-17 helper cells (Bettelli et al. 2006 *Nature* 441: 235-238).

The $T_H17$ pathway involving cytokine IL-17 has emerged to be a major participant in T cell-mediated sustained tissue damage (.Steinman. L. 2007 *Nature Med.* 13, 139-145). The pathway involves not only IL-17 but also cytokine IL-23, a heterodimeric molecule sharing the p40 subunit of $TH_1$ cytokine IL-12, but differs from IL-12 because of its distinctive p19 subunit. IL-23 drives a population of T-cells that produce IL-17, IL-6 and TNF (Furuzawa-Carballeda et al. 2007 *Autoimmun Rev* January; 6(3):169-175).

There is a body of evidence to suggest that dysregulation of T and B cell activity and response play a major role in inflammation as well as in autoimmunity. Importantly, the medicants of this invention are ribonucleotide reductase inhibitors. Ribonucleotide reductase catalyzes the reductive conversion of ribonucleotides to deoxynucleotides. This reductive reaction is a prime target for impeding cellular proliferation, and therefore amenable to controlling the quantity of T and B cells because it is a rate limiting step in the biochemical pathway leading to DNA synthesis and thus cell replication. DNA synthesis cannot occur without invoking this reaction since the endogenous pools of dNTP in mammalian cells are inadequate to support new DNA synthesis. It has been shown that rate of uncontrolled cell growth is closely associated with the specific activity of this enzyme. Members of this class of compounds have the ability to down regulate the expression of inflammatory cytokines produced by B and T cells, TNF α, IL-1, IL-6, IL-10, IL-12, and particularly IL-17. The IL-17/IL-23 pathway plays a major role in promoting and maintaining late tissue damage. Thus ribonucleotide reductase inhibitors should serve as novel therapeutic agents in treating neuroinflammatory and autoimmune disorders.

SUMMARY

Disclosed herein are ribonucleotide reductase inhibitors that can be used to prophylactically treat one or more autoimmune diseases or neuroinflammatory diseases, inter alia, multiple sclerosis. The disclosed ribonucleotide reductase inhibitors can also be used to prevent the onset of or the increased severity of one or more autoimmune diseases or neuroinflammatory diseases, inter alia, multiple sclerosis. Further disclosed are compositions comprising an effective amount of one or more ribonucleotide reductase inhibitors, the compositions useful for treating and/or preventing release of pro-inflammatory cytokines or for treating and/or preventing one or more autoimmune diseases or neuroinflammatory diseases, inter alia, multiple sclerosis.

DETAILED DESCRIPTION

Figure 1:
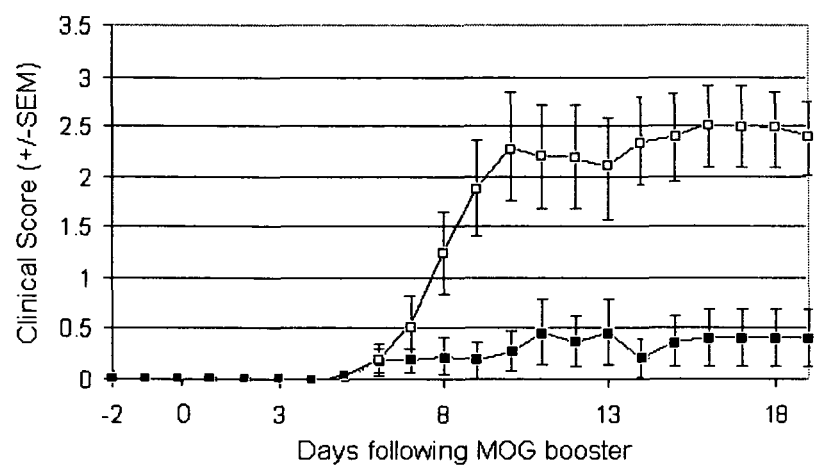
FIG. 1 depicts the ability of N,3,4-trihydroxybenzamide (Didox) to protect C57BL/6 mice from developing neuromuscular symptoms when the animals have been treated to induce experimental autoimmune encephalomyelitis (EAE). The line indicated with open squares (☒) represents the control animals which manifest EAE symptoms 5-7 days post MOG booster and continue to develop symptoms. The line indicated with solid squares (■) represents animals treated with N,3,4-trihydroxybenzamide two days prior to MOG booster (day-2) according to Example 1.

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Treatment" or "treating" means to administer a composition to a subject or a system with an undesired condition (e.g., neuroinflammation or autoimmune disease). The condition can include a disease. "Prevention" or "preventing" means to administer a composition to a subject or a system at risk for the condition. The condition can include a predisposition to a disease. The effect of the administration of the composition to the subject can have the effect of but is not limited to reducing or preventing the symptoms of the condition, a reduction in the severity of the condition, or the complete ablation of the condition.

By "effective amount" is meant a therapeutic amount needed to achieve the desired result or results, e.g., treating or preventing neuroinflammation or autoimmune diseases.

By "subject" is meant an individual. The subject can be a mammal such as a primate or a human. The term "subject" can include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

By "ribonucleotide reductase inhibitor" is meant any compound that impairs the enzyme ribonucleotide reductase that catalyzes the reductive reaction that converts ribonucleotides into deoxyribonucleotides. This reaction primarily occurs at the diphosphate form of the nucleotides.

The following chemical hierarchy is used throughout the specification to describe and enable the scope of the present invention and to particularly point out and distinctly claim the units which comprise the compounds of the present invention, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units may comprise only carbon atoms in the ring (carbocyclic and aryl rings) or may comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:

For the purposes of the present invention the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:

For the purposes of the present invention the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).

ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:

i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methyl-pyridinyl ($C_5$), and 4-dimethylaminopyridinyl ($C_5$)

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

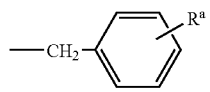

1. wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

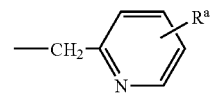

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present invention carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present invention, and to provide consistency in defining the present invention, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

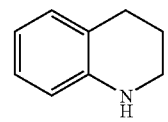

is, for the purposes of the present invention, considered a heterocyclic unit. 6,7-Dihydro-5H-cyclopentapyrimidine having the formula:

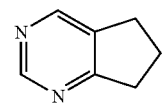

is, for the purposes of the present invention, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthyridine having the formula:

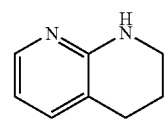

is, for the purposes of the present invention, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein below;

v) substituted or unsubstituted $C_1$-$C_9$ heteroaryl rings; as described herein below;

vi) —$(CR^{102a}R^{102b})_zOR^{101}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

vii) —$(CR^{102a}R^{102b})_zC(O)R^{101}$; for example, —COCH$_3$, —CH$_2$COCH$_3$, —OCH$_2$CH$_3$, —CH$_2$COCH$_2$CH$_3$, —COCH$_2$CH$_2$CH$_3$, and —CH$_2$COCH$_2$CH$_2$CH$_3$;

viii) —$(CR^{102a}R^{102b})_zC(O)OR^{101}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;

ix) —$(CR^{102a}R^{102b})_zC(O)N(R^{101})_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;

x) —$(CR^{102a}R^{102b})_zN(R^{101})_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;

xi) halogen; —F, —Cl, —Br, and —I;

xii) —$(CR^{102a}R^{102b})_zCN$;

xiii) —$(CR^{102a}R^{102b})_zNO_2$;

xiv) —$CH_jX_k$; wherein X is halogen, the index j is an integer from 0 to 2, j+k=3; for example, —CH$_2$F, —CHF$_2$, —CF$_3$, —CCl$_3$, or —CBr$_3$;

xv) —$(CR^{102a}R^{102b})_zSR^{101}$; —SH, —CH$_2$SH, —SCH$_3$, —CH$_2$SCH$_3$, —SC$_6$H$_5$, and —CH$_2$SC$_6$H$_5$;

xvi) —$(CR^{102a}R^{102b})_zSO_2R^{101}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xvii) —$(CR^{102a}R^{102b})_zSO_3R^{101}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each $R^{101}$ is independently hydrogen, substituted or unsubstituted $C_1$-$C_4$ linear, branched, or cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or branched alkyl; the index z is from 0 to 4

For the purposes of the present disclosure the terms "compound," "analog," and "composition of matter" stand equally well for the ribonucleic reductase inhibitors described herein, including all enantiomeric forms, diastereomeric forms, salts, and the like, and the terms "compound," "analog," and "composition of matter" are used interchangeably throughout the present specification.

The ribonucleotide reductase inhibitors disclosed herein include all salt forms, for example, salts of both basic groups, inter alia, amines, as well as salts of acidic groups, inter alia, carboxylic acids. The following are non-limiting examples of anions that can form salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: sodium, lithium, potassium, calcium, magnesium, bismuth, and the like.

Ribonucleotide Reductase Inhibitors

Disclosed herein are ribonucleotide reductase inhibitors having the formula:

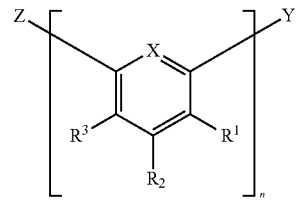

wherein the index n is 0 or 1;
X is N or CR;
R is chosen from hydrogen and hydroxyl;
Y is a unit having the formula:

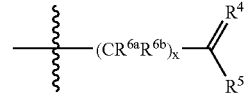

$R^4$ is chosen from:
i) O;
ii) S; or
iii) $NR^7$:
$R^7$ is chosen from:
i) hydrogen;
ii) hydroxy;
iii) amino
iv) cyano;
v) substituted or unsubstituted $C_1$-$C_4$ linear or branched alkyl;
vi) substituted or unsubstituted $C_1$-$C_4$ linear or branched alkoxy; or
vii) $NR^8R^9$; $R^8$ and $R^9$ are each independently chosen from hydrogen, hydroxy, amino, $C_1$-$C_4$ linear or branched alkyl, $C_1$-$C_4$ linear or branched alkoxy, or $C(=R^{10})R^{11}$; $R^{10}$ is chosen from O, S, or $NR^{12}$; $R^{12}$ is hydrogen, hydroxyl, or amino; $R^{11}$ is chosen from hydrogen, hydroxyl, amino, cyano, $C_1$-$C_4$ linear or branched alkyl, or $C_1$-$C_4$ linear or branched alkoxy;
$R^5$ is chosen from:
i) hydrogen;
ii) hydroxy;
iii) cyano;
iv) substituted or unsubstituted $C_1$-$C_{10}$ linear or branched alkyl;
v) substituted or unsubstituted $C_1$-$C_{10}$ linear or branched alkoxy;
vi) substituted or unsubstituted phenoxy; or
vii) $NR^{13}R^{14}$; $R^{13}$ and $R^{14}$ are each independently chosen from hydrogen, hydroxy, amino, $C_1$-$C_4$ linear or branched alkyl, $C_1$-$C_4$ linear or branched alkoxy, or $C(=R^{15})R^{16}$; $R^{15}$ is chosen from O, S, or $NR^{17}$; $R^{17}$ is hydrogen, hydroxyl, or amino; $R^{16}$ is chosen from hydrogen, hydroxyl, amino, cyano, $C_1$-$C_4$ linear or branched alkyl, or $C_1$-$C_4$ linear or branched alkoxy;
$R^{6a}$ and $R^{6b}$ are each independently hydrogen, hydroxy, amino, $C_1$-$C_4$ linear or branched alkyl, or $C_1$-$C_4$ linear or branched alkoxy;
the index x is 0 or 1;
Z is chosen from:
i) hydrogen;
ii) hydroxyl;
iii) $NR^{18a}R^{18b}$; $R^{18a}$ and $R^{18b}$ are each independently chosen from hydrogen, hydroxy, amino, $C_1$-$C_6$ linear or branched alkyl, $C_1$-$C_6$ linear or branched alkoxy, or $C(=R^{21})R^{22}$; $R^{21}$ is chosen from O, S, or $NR^{23}$; $R^{23}$ is hydrogen, hydroxyl, or amino; $R^{22}$ is chosen from hydrogen, hydroxyl, amino, cyano, $C_1$-$C_6$ linear or branched alkyl, or $C_1$-$C_6$ linear or branched alkoxy;
iv) $NR^{19}NR^{20a}R^{20b}$; $R^{19}$, $R^{20a}$, and $R^{20b}$ are each independently chosen from hydrogen, hydroxy, amino, $C_1$-$C_6$ linear or branched alkyl, $C_1$-$C_6$ linear or branched alkoxy, or $C(=R^{21})R^{22}$; $R^{21}$ is chosen from O, S, or $NR^{23}$; $R^{23}$ is hydrogen, hydroxyl, or amino; $R^{22}$ is chosen from hydrogen, hydroxyl, amino, cyano, $C_1$-$C_6$ linear or branched alkyl, or $C_1$-$C_6$ linear or branched alkoxy;
v) substituted or unsubstituted $C_1$-$C_6$ linear or branched alkyl;
vi) substituted or unsubstituted $C_1$-$C_6$ linear or branched alkoxy;
vii) —$C(O)OR^{24}$; $R^{24}$ is hydrogen, substituted or unsubstituted $C_1$-$C_6$ alkyl, substituted or unsubstituted phenyl;
viii) —$OC(O)R^{25}$; $R^{25}$ is substituted or unsubstituted $C_1$-$C_6$ alkyl or substituted or unsubstituted phenyl;
ix) substituted or unsubstituted $C_6$ or $C_{10}$ aryl;
x) substituted or unsubstituted $C_1$-$C_9$ heterocyclic;
xi) substituted or unsubstituted $C_1$-$C_9$ heteroaryl; and
$R^1$, $R^2$, and $R^3$ are each independently chosen from:
i) hydrogen;
ii) hydroxyl;
iii) amino;
iv) halogen;
v) substituted or unsubstituted $C_1$-$C_3$ alkyl;
vi) substituted or unsubstituted $C_1$-$C_3$ alkoxy;
vii) —$C(O)OR^{26}$; $R^{26}$ is hydrogen, substituted or unsubstituted $C_1$-$C_6$ alkyl, substituted or unsubstituted phenyl;
viii) —$OC(O)R^{27}$; $R^{27}$ is substituted or unsubstituted $C_1$-$C_6$ alkyl or substituted or unsubstituted phenyl;
ix) —$NR^{28}NR^{29}R^{30}$; $R^{28}$ is hydrogen or $C_1$-$C_3$ alkyl, $R^{29}$ and $R^{30}$ are each independently chosen from hydrogen or $C_1$-$C_3$ alkyl; or
x) $R^1$ and $R^2$ can be taken together to form a substituted or unsubstituted 6-member aryl ring.

When the index n is 0, the disclosed inhibitors have the formula:

Z—Y.

Non-limiting examples of categories included within this disclosure include:

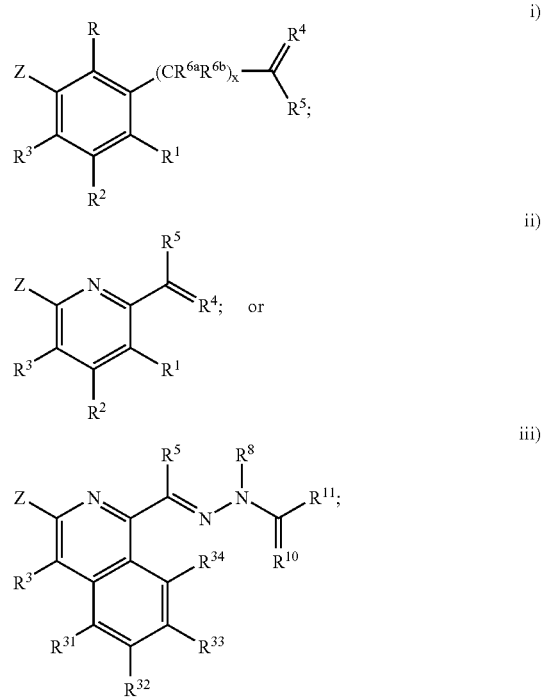

wherein $R^{31}$, $R^{32}$ $R^{33}$, and $R^{34}$ are each independently chosen from substitution independently chosen from:
i) hydrogen;
ii) $C_1$-$C_{12}$ linear, branched, or cyclic alkyl, alkenyl, and alkynyl;
iii) substituted or unsubstituted $C_6$ or $C_{10}$ aryl;
iv) substituted or unsubstituted $C_6$ or $C_{10}$ alkylenearyl;
v) substituted or unsubstituted $C_1$-$C_9$ heterocyclic rings;
vi) substituted or unsubstituted $C_1$-$C_9$ heteroaryl rings;
vii) —$(CR^{102a}R^{102b})_zOR^{101}$;
viii) —$(CR^{102a}R^{102b})_zC(O)R^{101}$;

ix) —$(CR^{102a}R^{102b})_zC(O)OR^{101}$;
x) —$(CR^{102a}R^{102b})_zC(O)N(R^{101})_2$;
xi) halogen;
xii) —$(CR^{102a}R^{102b})_zCN$;
xiii) —$(CR^{102a}R^{102b})_zNO_2$;
xiv) —$(CH_jX_k)$; wherein X is halogen, j is from 0 to 2, j+k=3;
xv) —$(CR^{101a}R^{102b})_zSR^{101}$;
xvi) —$(CR^{102a}R^{102b})_zSO_2R^{101}$; and
xvii) —$(CR^{102a}R^{102b})_zSO_3R^{101}$;

wherein each $R^{101}$ is independently hydrogen, substituted or unsubstituted $C_1$-$C_4$ linear, branched, or cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or branched alkyl; the index z is from 0 to 4.

One aspect of the disclosed ribonucleotide reductase inhibitors relates to compounds having the formula:

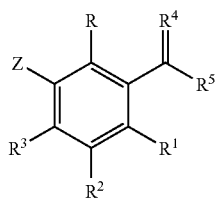

wherein $R^4$ is chosen from:
i) O;
ii) NH; or
iii) NOH;
$R^5$ is chosen from:
i) OH;
ii) $C_1$-$C_4$ linear or branched alkyl;
iii) $NH_2$;
iv) NHOH; or
v) $NHNH_2$;
Z, R, $R^1$, $R^2$, and $R^3$ are each independently hydrogen or hydroxyl.

One iteration of this aspect relates to 2,3-dihydroxyphenyl compounds, non-limiting examples of which include:

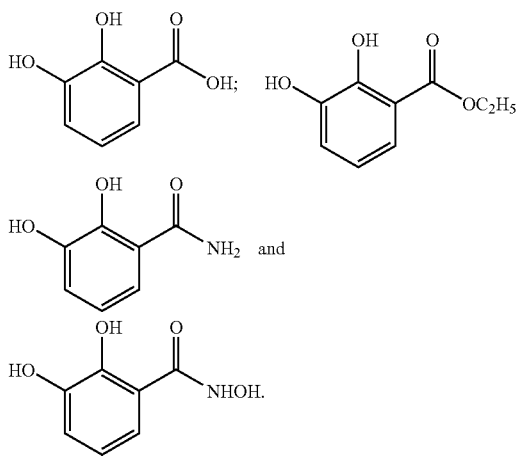

A further iteration of this aspect relates to 3,4-dihydroxyphenyl compounds, non-limiting examples of which include:

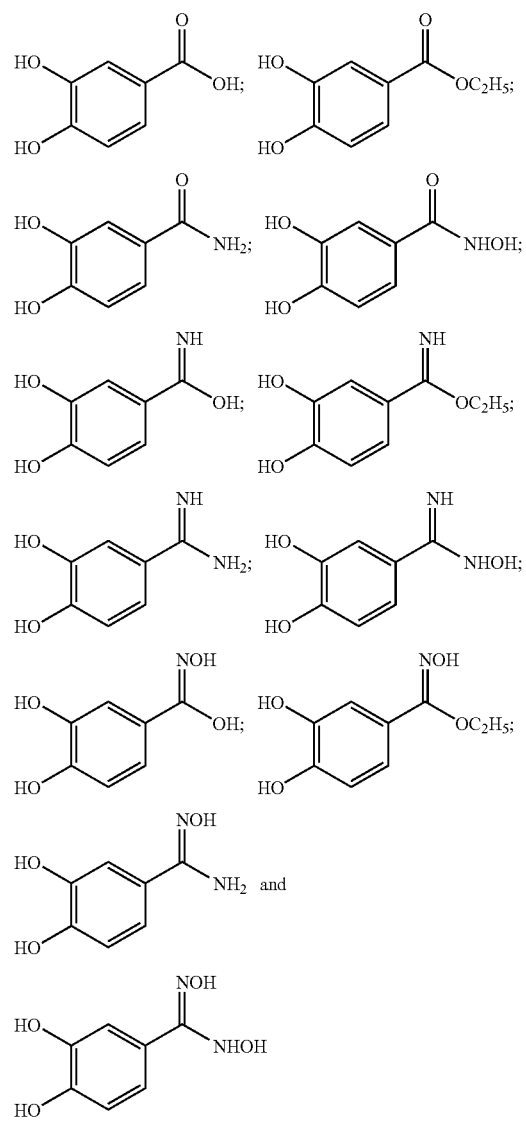

Another iteration of this aspect relates to 3,4,5-trihydroxyphenyl compounds, non-limiting examples of which include:

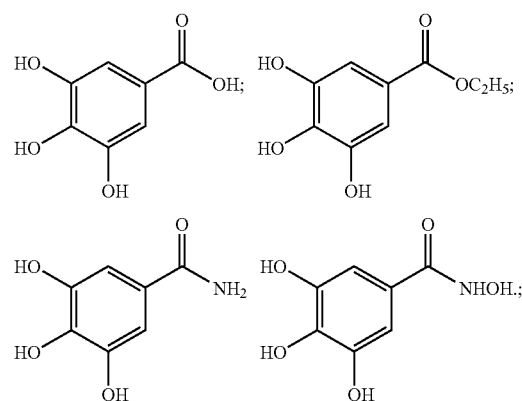

-continued

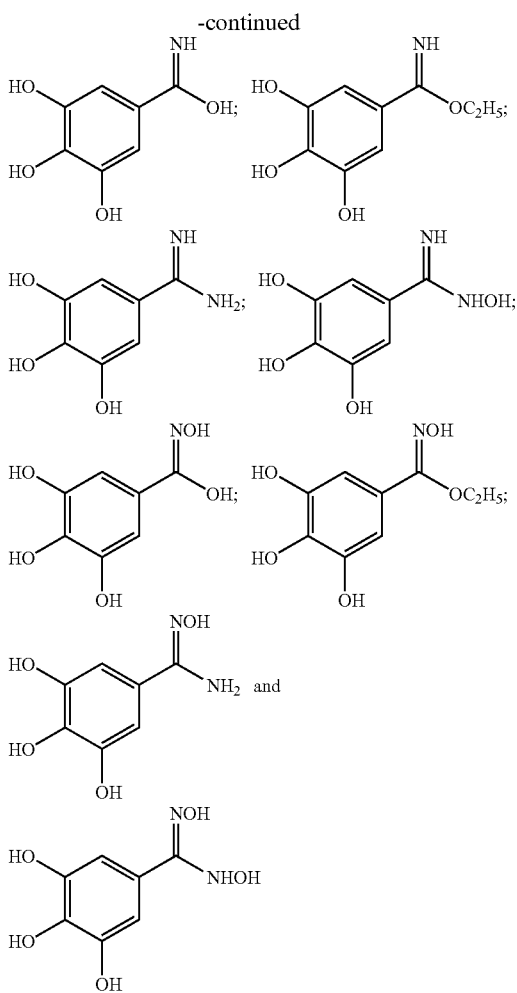

Another aspect of the disclosed ribonucleotide reductase inhibitors relates to compounds having the formula:

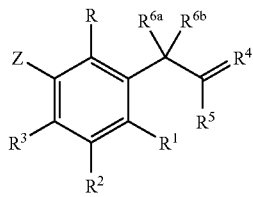

Y is a unit having the formula:

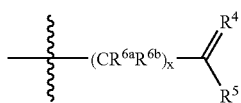

wherein $R^4$ is chosen from:
iv) O;
v) NH; or
vi) NOH;
$R^5$ is chosen from:
i) OH;
ii) $C_1$-$C_4$ linear or branched alkyl;
iii) $NH_2$;
iv) NHOH; and
v) $NHNH_2$;

Z, R, $R^1$, $R^2$, and $R^3$ are each independently hydrogen or hydroxyl; and $R^{6a}$ and $R^{6b}$ are each independently chosen from hydrogen, methyl, and hydroxyl.

One embodiment of this aspect relates to phenols having the formula:

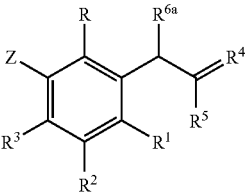

wherein R, $R^1$, $R^2$, $R^3$, and Z are each independently hydrogen or hydroxy; $R^4$ is =O, =NH or =NOH; $R^5$ is —H or —OH; R is —$NH_2$, —NHOH, $C_1$-$C_3$ alkoxy, or phenoxy; and $R^{6a}$ is hydrogen or methyl.

The following are non-limiting iterations of this embodiment:

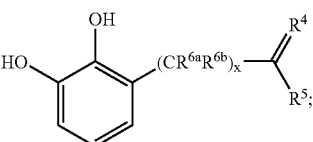

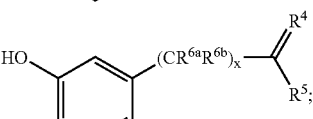

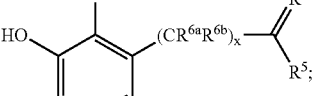

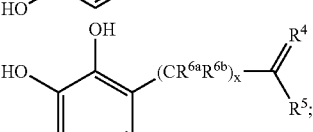

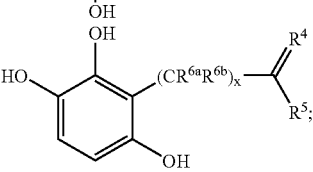

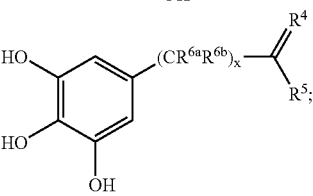

-continued

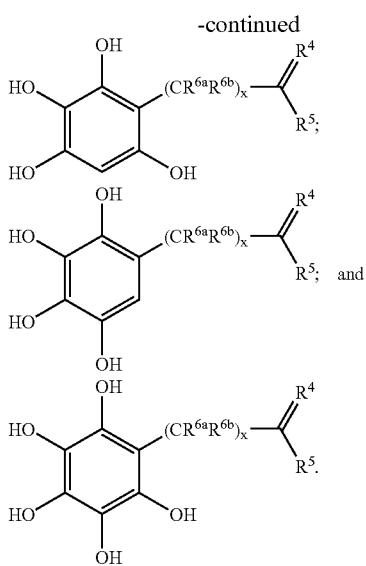

Further iterations relate to ribonucleotide reductase inhibitors having the formulae:

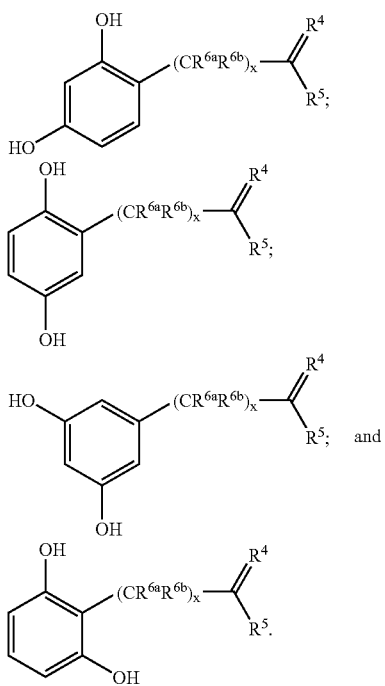

Yet further described herein are ribonucleotide reductase inhibitors for the treatment or prevention of neuroinflammation or autoimmune diseases. In one aspect, the ribonucleotide reductase inhibitors useful herein have the formula I

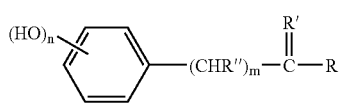

I wherein n is from 2 to 5, m is 0 or 1, R is $NH_2$, NHOH, $OC_{1-3}$ alkyl or O-phenyl, R' is O, NH or NOH and R" is H or OH. In another aspect, prodrugs of the compounds having the formula I can be used. For example, phenolic acetyl derivatives of compounds according to formula I can be used as the ribonucleotide reductase inhibitors. In this aspect, the acetyl derivatives act as "pro-drugs" in that they are converted by the subject to the corresponding ribonucleotide reductase inhibitor having entirely unesterified phenolic hydroxyls, which are the therapeutically active drugs.

Examples of ribonucleotide reductase inhibitors covered under formula I include, but are not limited to, 2,3-dihydroxyphenyl, 3,4-dihydroxyphenyl, 2,5-dihydroxyphenyl, 2,6-dihydroxyphenyl, 2,3,4-trihydroxyphenyl, 2,3,5-trihydroxyphenyl, 3,4,5-trihydroxyphenyl, 2,4,5-trihydroxyphenyl, 2,3,4,5-tetrahydroxyphenyl, pentahydroxyphenyl and the like groups.

In one aspect, when the ribonucleotide reductase inhibitor has the formula 1, m is I and R" is H (a phenylacetic acid derivative). In another aspect, when the ribonucleotide reductase inhibitor has the formula I, m is 1 and R" is OH (a mandelic acid derivative). In a further aspect, when the ribonucleotide reductase inhibitor has the formula I, m is 0, R is NHOH and R' is O (an N-hydroxybenzamide (formerly, a benzohydroxamic acid)). In another aspect, when the ribonucleotide reductase inhibitor has the formula I, R is $NH_2$ and R' is NH (a benzimidamide (formerly a benzamidine)). In a further aspect, when the ribonucleotide reductase inhibitor has the formula I, R is NHOH and R' is NH (an N-hydroxy benzimidamide (formerly a benzamidoxime)). In another aspect, when the ribonucleotide reductase inhibitor has the formula I, R is NHOH and R' is NOH (an N,N'-dihydroxy benzimidamide (formerly, a hydroxyamidoxime)). In a further aspect, when the ribonucleotide reductase inhibitor has the formula I, R is O-alkyl or O-phenyl and R' is NH (a benzimidate). In another aspect, when the ribonucleotide reductase inhibitor has the formula I, R is $OC_{1-10}$ alkyl, wherein the alkyl groups include, but are not limited to, methyl, ethyl, isopropyl and n-propyl.

Compounds represented by formula I are disclosed in U.S. Pat. Nos. 6,248,782; 4,253,322; 4,623,659; 2,848,430 and 3,629,443, which are incorporated by reference in their entireties. Methods for their preparation are also fully disclosed in these patents as well as in the many references cited therein.

In another aspect, ribonucleotide reductase inhibitors having the formula II can be used in the methods described herein

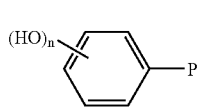

II wherein n is from 2 to 5 and P can be COOH or the pharmaceutically-acceptable salt or ester thereof, CN, $C_1$-$C_8$ alkyl, aryl-substituted $C_1$-$C_8$ alkyl, acylamino, $HOC_2H_4$—NH—$CH_2$—C(=O)—, $C_1$-$C_2H_4$—$NCH_3$—$CH_2$—C(=O)—, $C(S)OC_2H_5$, C(O)—NH—$C_{1-3}$ alkyl, C(=NH)—N(OH)—$C_{1-3}$ alkyl and substituted variants thereof. In one aspect, phenolic blocking groups such as, for example, alkanoic acids, phenacyl esters and the like can be employed to yield pro-drugs which are removed by the subject upon administration to yield drugs containing only free phenolic hydroxyls.

In another aspect, ribonucleotide reductase inhibitors useful herein have the formula $R_{31}Z$, wherein $R_{31}$ can be H, $NH_2$, $NH_2$—NH, NHOH, NOH—$R^{36}$, $C_1$-$C_6$ alkyl $OC_{1-6}$alkyl, aryl-substituted with $C_1$-$C_6$ alkyl, phenyl, naphthyl, pyridyl, pyrimidyl or thienyl, and wherein Z can be C(=O)NOH—$R^{34}$, C(=S)—NOH—$R^{34}$, C(=NH)—NOH—$R^{34}$, C(=NOH)—$C_1$-$C_3$ alkyl, C(=NOH)—$R^{34}$ and C(=NOH)—$R^{45}$, wherein $R^{34}$ can be H, $C_1$-$C_6$ alkyl and substituted $C_1$-$C_6$ alkyl, wherein $R^{34}$ can be substituted with hydroxy, alkoxy, amino or halo, and wherein $R^{35}$ is $NH_2$ or NHOH, wherein $R^{36}$ is $C_{1-6}$ acyl, alkyl and substituted $C_{1-6}$ alkyl substituted with hydroxyl, alkoxy, amino or halo and the like. The above groups of compounds are generally referred to as "hydroxyureas." The compounds disclosed in CANCER RES. 27 (Part 1) 635 (1967) by Young et al., which is incorporated by reference in its entirety, can be used herein. In one aspect, the ribonucleotide reductase inhibitors can be hydroxyurea.

In another aspect, ribonucleotide reductase inhibitors useful in the methods herein include semithiocarbazones such as, for example, 2-formylpiperidine, 2-acetylpyridine, 1-formylisoquinoline, 1-acetylisoquinoline, and their ring substituted analogs. Formulae III and IV below illustrate these compounds

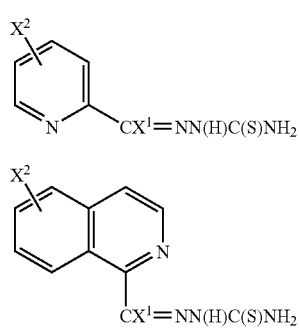

wherein Formula III represents pyridine-type compounds and Formula IV represents isoquinoline-semithiocarbazones, where $X^1$ can be H or $CH_3$, $X^2$ can be H, OH, $NH_2$, F, $CF_3$, $C_{1-3}$alkyl, $OX^3$, $NHX^3N(X^3)_2$, and $O(O=C)X^4$, in which $X^3$ denotes $C_{1-3}$ alkyl and $X^4$ can be aryl, $C_{1-6}$ alkyl including substitutions on the alkyl chain of the carboxylic acid with $C_{1-3}$ alkoxy, $C_{1-3}$ mono- or di-alkylamino, aryloxy, also those in which the aryl ring is substituted with one or more hydroxy, amino or chloro groups. Both E and Z isomers of the compounds and their mixtures can be used herein.

In one aspect, 2-formylpyridine and 2-acetylpyridine thiosemicarbazone derivatives useful herein include 3-hydroxy, 3-amino, 3-methyl, 3-methoxy, 3-acetoxy, 3-ethoxy, 3-fluoro, 5-hydroxy, 5-amino, 5-fluoro, 5-trifluoromethyl, 5-methoxy, 5-ethoxy, 5-dimethylamino, 5-pivaloyloxy, 5-phenoxyacetoxy, 5-N, N-dimethylaminoacetoxy, and 3,4-dihydroxybenzoyloxy as ring substituents. In another aspect, 1-formylisoquinoline and 1-acetylisoquinoline thiosemicarbazone derivatives useful herein include 4-hydroxy, 4-methyl, 4-amino, 5-fluoro, 5-trifluoromethyl, 5-amino and 5-acetylamino as ring substituents. The 2-formylpyridine and 1-formylisoquinoline thiosemicarbazone derivatives disclosed in French et al, J. Med. Chem. 17:172 (1974), which is incorporated by reference in its entirety, can be used herein.

In another aspect, the polyphenolic compounds N-3,4-trihydroxybenzamide (Didox) and ethyl-3,4,5-trihydroxybenzenecarboximidate-HCl (Imidate) can be used herein as ribonucleotide reductase inhibitors.

The following are non-limiting examples of the preparation of ribonucleotide reductase inhibitors according to this aspect.

Example I

Preparation of 3,4-dihydroxybenzamidoxime: To a 500 mL flask containing hydroxylaminesulfate (25 g, 0.19 mol), which has was neutralized by the addition of aqueous sodium hydroxide to a pH of approximately 8.0 in water (300 mL), is charged 3,4-Dihydroxybenzonitrile (30 g, 0.22 mol). The reaction mixture was stirred at approximately 45° C. for 18 hours. The desired product, 3,4-dihydroxybenzamidoxime precipitated out of solution and was collected by filtration. The crude product was suspended in water and the aqueous suspension acidified to approximately pH 2.0 with 12N aqueous hydrochloric acid. The acidic solution was decolorized with charcoal and the solvent removed by evaporation. Recrystallization of the residue afforded 3,4-dihydroxybenzamidoxime hydrochloride (72% yield). M.p. 193° C. (dec.). Analysis Calculated: C, 41.09; H, 4.43; N, 13.69. Found: C, 41.12; H, 4.47; N, 13.69.

Example II

Preparation of N,3,4,5-tetrahydroxybenzenecarboximidamide (Trimidox): About 7.5 g. of 3,4,5-trihydroxybenzonitrile were dissolved in 200 ml. of water containing 7 g. of hydroxylamine sulfate which solution had previously been neutralized to about pH=8.0 with aqueous sodium hydroxide. 2 g. of sodium sulfite were also present in solution. The reaction mixture was stirred at 45° C. for about 18 hours after which time the precipitated N,3,4,5-tetrahydroxybenzenecarboximidamide formed in the above reaction was collected. The product was converted to the hydrochloride salt and the hydrochloride salt purified by the process of Example 1. N,3,4,5-tetrahydroxybenzenecarboximidamide hydrochloride thus prepared melted with decomposition at a temperature of about 206° C. after recrystallization from an isopropanol-ethyl acetate solvent mixture. Analysis Calculated: C, 38.11; H, 4.11; N, 12.72. Found: C, 38.16; H, 4.16; N, 12.66. Equivalent weight by titration with aqueous sodium hydroxide=220 (theory=220.6); yield=80%.

Example III

Preparation of Ethyl 3,4,5-Trihydroxybenzenecarboximidate: 5 g. of 3,4,5-Trihydroxybenzonitrile were dissolved in ether. 2.2 mL of ethanol were added. Next, anhydrous gaseous hydrogen chloride was passed through the solution. Ethyl 3,4,5-trihydroxybenzenecarboxmidate hydrochloride formed in the above reaction precipitated. The precipitate was recrystallized from an isopropanolether solvent mixture. Ethyl 3,4,5-trihydroxybenzenecarboximidate hydrochloride thus prepared and purified melted at about 72° C. with decomposition. Analysis Calculated: C, 46.26; H, 5.18; N, 5.99. Found: C, 46.26; H, 5.22; N, 6.00. Equivalent weight by titration with sodium hydroxide=115.5 (theory=116.8); yield=78%. Ethyl 3,4,5-trihydroxybenzenecarboximidate can be prepared by neutralization of the hydrochloride salt, extraction of the ester into ether and removal of the ether by evaporation.

Example IV

Preparation of Ethyl 3,4-Dihydroxybenzamidate: Following the procedure of Example III, 3,4-dihydroxybenzonitrile was converted to ethyl 3,4-dihydroxybenzamidate hydrochloride by the reaction with ethanol in the presence of hydrogen chloride. The compound melted at 170° C. with decomposition after recrystallization from an isopropanol/ether solvent mixture; yield=65%. Analysis Calculated: C, 49.67; H, 5.66; N, 6.44. Found: C, 49.91; H, 5.61; N, 6.45.

Example V

Preparation of Gallamidine: About 4.5 g. of ethyl 3,4,5-trihydroxybenzamidate hydrochloride were heated with an excess of 14N aqueous ammonium hydroxide in ethanol solution. The volatile constituents were removed by evaporation and the residue, comprising gallamidine formed in the above reaction, was dissolved in alcohol. Gallamidine free base was converted to the hydrochloride salt by passing gaseous hydrogen chloride into the alcoholic solution. Gallamidine hydrochloride melted at about 169° C. with decomposition after recrystallization from an ethanol/ethyl acetate solvent mixture; yield=53%. Equivalent weight=203 by titration with aqueous sodium hydroxide (theory 204.5). Analysis Calculated: C, 41.09; H, 4.43; N, 13.69. Found: C, 40.80; H, 4.47; N, 14.30.

Example VI

Preparation of 3,4-Dihydroxybenzohydroxyamidoxime. A solution of 5.5 g. of 3,4-dihydroxybenzamidoxime (from Example 1) was prepared in a minimal quantity of methanol. 3.5 g. of hydroxylamine hydrochloride were added. The reaction mixture was allowed to stand for about one day at about 50° C. Volatile constituents were removed by evaporation. Ethyl acetate was added to the residue. The resulting precipitate was separated by filtration and gaseous hydrogen chloride passed into the filtrate. 3,4-Dihydroxybenzohydroxyamidoxime hydrochloride thus prepared was separated by filtration. The compound melted at about 169° C. with decomposition. Equivalent weight by titration with sodium hydroxide=219 (theory=220.5) Analysis Calculated: C, 38.11; H, 4.11; N, 12.70. Found: C, 38.28; H, 4.15; N, 12.61.

Another aspect of the disclosed inhibitors relates to compounds having the formula:

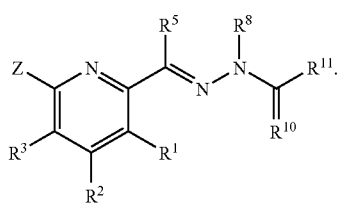

In one embodiment, $R^5$ is hydrogen or methyl $R^8$ is hydrogen or methyl, $R^{10}$ is S; $R^{11}$ is $NH_2$; $R^1$ is chosen from hydrogen, methyl, methoxy, ethoxy, hydroxy, acetate, fluoro, chloro, and carboxy; $R^3$ is chosen from hydrogen, halogen, hydroxy, substituted or unsubstituted $C_1$-$C_4$ alkyl, and substituted or unsubstituted $C_1$-$C_4$ alkoxy. In one iteration, $R^3$ is chosen from hydrogen, fluoro, chloro, hydroxy, methoxy, ethoxy, 2-dimethylaminoethoxy, and 2-(ethoxyethoxy)ethoxy. In a further iteration, $R^3$ is a unit having the formula:

—OC(O)$R^{25}$ wherein $R^{25}$ is a substituted or unsubstituted alkyl unit chosen from methyl, ethyl, propyl, tert-butyl, methoxymethyl, ethoxymethyl, trifluoromethyl, (dimethylamino)methyl, phenoxy-methyl, (2-chlorophenoxy)methyl, (4-chlorophenoxy)methyl, (2,4-dichlorophenoxy)methyl, and (2,4,5-trichlorophenoxy)methyl.

Another aspect relates to ribonucleotide reductase inhibitors having the formula:

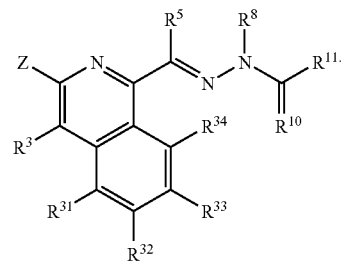

wherein Z, $R^3$, $R^5 R^8$, $R^{10}$, and $R^{11}$ are the same as defined herein above, and $R^{31}$, $R^{32}$ $R^{33}$, and $R^{34}$ are each independently chosen from hydrogen, methyl, methoxy, ethoxy, hydroxy, cyano, acetate, fluoro, chloro, and carboxy.

In one iteration, $R^5$ is hydrogen or methyl; $R^8$ is hydrogen or methyl; $R^{10}$ is S; $R^{11}$ is $NH_2$; and $R^{31}$, $R^{32}$ $R^{33}$, and $R^{34}$ are each independently chosen from hydrogen, methyl, methoxy, ethoxy, hydroxy, cyano, acetate, fluoro, chloro, and carboxy. Non-limiting examples of this iteration include inhibitors wherein $R^{31}$ is chosen from hydrogen, fluoro, chloro, hydroxy, methoxy, ethoxy, 2-dimethylaminoethoxy, and 2-(ethoxyethoxy)ethoxy. A further iteration relates to $R^{31}$ units having the formula:

—OC(O)$R^{25}$ wherein $R^{25}$ is a substituted or unsubstituted alkyl unit chosen from methyl, ethyl, propyl, tert-butyl, methoxymethyl, ethoxymethyl, trifluoromethyl, (dimethylamino)methyl, phenoxy-methyl, (2-chlorophenoxy)methyl, (4-chlorophenoxy)methyl, (2,4-dichlorophenoxy)methyl: and (2,4,5-trichlorophenoxy)methyl.

The inhibitors according to this aspect can be prepared by the procedure disclosed by French F. A. et al., "α-(N)-Formylheteroaromatic Thiosemicarbazones. Inhibition of Tumor-Derived Ribonucleoside Diphosphate Reductase and Correlation with in Vivo Antitumor Activity," *Journal of Medicinal Chemistry*, 1974, Vol. 17, No. 2 pg 172 which is incorporated herein by reference in its entirety.

Another aspect of the disclosed ribonucleotide reductase inhibitors relates to inhibitors having the formula:

Z—Y;

wherein Z is chosen from:
i) hydrogen;
ii) $NH_2$;
iii) $NHNH_2$;
iv) NHOH;
i) NOH$R^{18b}$; $R^{18b}$ is chosen from substituted or unsubstituted $C_1$-$C_6$ linear or branched alkyl, $C_1$-$C_6$ linear or branched alkoxy, or C(=O)$R^{22}$; $R^{22}$ is $C_1$-$C_6$ linear or branched alkyl;
ii) substituted or unsubstituted $C_1$-$C_6$ linear or branched alkyl;
iii) phenyl;
iv) naphthyl;
v) pyridinyl;

vi) pyrimidinyl; or
vii) thienyl; and
Y has the formula:

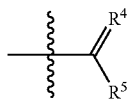

R⁴ is chosen from:
i) O;
ii) S; or
NHR⁷; R⁷ is chosen from hydrogen, hydroxy, amino, substituted or unsubstituted $C_1$-$C_4$ linear or branched alkyl; or substituted or unsubstituted $C_1$-$C_4$ linear or branched alkoxy.

Non-limiting examples of inhibitors according to this aspect include inhibitors chosen from hydroxylamine, methoxyamine, N-methylhydroxylamine, O,N-dimethylhydroxyl-amine, formamidoxime, N-hydroxyglycine, N-hydroxyglycine amide, acetohydroxamic acid, N-methylacetohydroxamic acid, hydroxyurea, methoxyurea, 1-methoxy-1-methyl urea, N-ethylhydroxyurea, N-acetylhydroxyurea, 3-phenyl-1-hydroxyurea, dihydroxyurea, N-hydroxy-urethane, N-hydroxyguanidine, guanidine, and 3-phenyl-1-hydroxy-2-thiourea.

Methods

In one aspect, disclosed are methods for treating or preventing neuroinflammatory or autoimiune disease in a subject, comprising administering to the subject an effective amount of a ribonucleotide reductase inhibitor. In one aspect, ribonucleotide reductase inhibitors can be used for the treatment of neuroinflammatory and autoimmune disease by controlling the quantity of T and B cells and the release of inflammatory cytokines.

Not wishing to be bound by theory, it is believed that ribonucleotide reductase inhibitors possess chemical and biological properties that can impair several processes that contribute to the neuroinflammatory and autoimmune disease process. For example, members of the polyphenolic series such as 3,4-dihydroxy- and 3,4,5-trihydroxy-compounds have been shown to be good anti-inflammatory agents by inhibiting NF-kappa B activation and, therefore, down regulating cytokines contributing to the inflammation process and chemoattractant production. Also these compounds can inhibit tissue factor production. This synergistic concept may be an approach to the prevention of neuroinflammatory and autoimmune disease by attenuating inflammatory reactions that contribute to the pathogenesis of these disorders.

The agents of this invention, for example, the polyhydroxy phenolic compounds, have the ability to modulate several of the important biological events contributing to the development of neuroinflammatory and autoimmune disease: T and B cell activation, leukocyte migration, NF-kappa B activation and tissue factor expression, down regulation of inflammatory cytokine production, particularly IL-17, contributors to inflammation. These compounds being excellent free-radical scavengers, are able to modulate the above-mentioned deleterious processes. Having these properties make these compounds unique to limit the inflammatory process.

Disclosed herein are methods for treating and/or preventing one or more autoimmune diseases, non-limiting examples of which include acute disseminated encephalomyelitis, Addison's disease, Ankylosing spondylitis, antiphospholipid antibody syndrome, autoimmune hemolytic anemia, autoimmune hepatitis, bullous pemphigoid, Coeliac disease, Dermatomyositis, Diambetis mellitus type 1, Goodpature's syndrome, Graves' disease, Guillain-Barré syndrome, Hashimoto's disease, Ideopathic thrombocytopenic purpura, interstitial cystitis, lupus erythematosus, multiple sclerosis, myasthenia gravis, pemphigus vulgaris, pernicious anaemia, polymyositis, primary biliary cirrhosis, rheumatoid arthritis, Sjögren's syndrome, temporal arteritis, vasculitis, and Wegener's granulomatosis comprising, contacting a patient in need of treatment with an effective amount of one or more of the disclosed ribonucleotide reductase inhibitors.

Further disclosed herein are methods for treating and/or preventing one or more neurodegenerative diseases, non-limiting examples of which include alcoholism, Alexander's disease, Alper's disease, Alzheimer's disease, amyotrophic lateral sclerosis, ataxia telangiectasia, traumatic brain injury, bovine spongiform encephalopathy, Canavan disease, Coackayne syndrome corticobasal degeneration, Creutzfeldt-Jakob disease, Huntington's disease, HIV-associated dementia, Kennedy's disease, Krabbe's disease, Lewy body dementia, spinocerebaellare ataxia type 3, multiple sclerosis, multiple system atrophy, narcolepsy, neuroborreliosis, Parkinson's disease, Pelizaeus-Merzbacher disease, Pick's disease, primary lateral sclerosis, Prion disease, progressive supranuclear palsy, Refsum's disease, Sandhoff's disease, Schilder's disease, subacute combined degeneration of spinal cord secondary to pernicious anaemia, schizophrenia, Spielmeyer-Vogt-Sjorgen-Batten disease, spinocerebellar ataxia, spinal muscular atrophy, Steel-Richardson-Olszewski disease, and tabes dorsalis comprising contacting a patient in need of treatment with an effective amount of one or more of the disclosed ribonucleotide reductase inhibitors.

Yet further herein are methods for treating and/or preventing one or more neurodegenerative diseases or autoimmune disease chosen from systemic lupus, inflammatory bowel disease, psoriasis, Crohn's disease, rheumatoid arthritis, sarcoid, Alzheimer's disease, insulin dependent diabetes mellitus, atherosclerosis, asthma, spinal cord injury, stroke, a chronic inflammatory demyelinating neuropathy, multiple sclerosis, a congenital metabolic disorder, a neuropathy with abnormal myelination, drug-induced demyelination, radiation induced demyelination, a hereditary demyelinating condition, a prion-induced demyelination, and encephalitis-induced demyelination.

Also disclosed herein are methods for treating and/or preventing an autoimmune disease or neurodegenerative disease, for example, those listed herein, wherein one or more of the disclosed ribonucleotide reductase inhibitors are administered to a patient in need in combination with one or more pharmaceutically active agents that are effective against multiple sclerosis. Examples of such agents include the interferons (interferon beta 1-a, beta 1-b, and alpha), glatiramer acetate or corticosteroids such as methylprednisolone and prednisone as well as chemotherapeutic agents such as mitoxantrone, methotrexate, azathioprine, cladribine cyclophosphamide, cyclosporine and tysabri.

Also disclosed herein are methods for treating and/or preventing a lipid storage disease, for example, sphingolipidosis, Fabry's disease, GM1 gagliosidoses, GM2 gangliosidosis, Tay-Sachs disease, Sandhoff disease, Gaucher's disease, Krabbe disease, Metachromatic leukodystrophy, and Niemann-Pick disease.

Further disclosed herein are methods for inhibiting in vivo, in vitro, and ex vivo the release of proinflammatory cytokines, comprising contacting tissue with an effective amount of one or more ribonucleotide reductase inhibitors described herein.

Also disclosed herein is the use of one or more ribonucleotide reductase inhibitors described herein for making a medicament for the treatment of a neuroinflammatory or autoimmune disease in a subject.

Still further disclosed herein are methods for treating multiple sclerosis (MS), comprising administering to a subject in need of treatment an effective amount of one or more ribonucleotide reductase inhibitors described herein.

Procedures

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

Example 1

Experimental Autoimmune Encephalomyelitis (EAE) Model Studies

One method of showing the efficacy of the disclosed compounds for the treatment of various conditions associated with multiple sclerosis (MS) is its ability to inhibit effects of Experimental Autoimmune Encephalomyelitis (EAE) in laboratory animals. EAE is an animal model for MS, which entails inducing a T-cell-mediated autoimmune disease against myelin basic protein in certain susceptible mammalian species. The EAE model is an appropriate method for studying the inflammation of the brain and spinal cord associated with MS (see Bolton, C. *Mult. Scler.* 1995; 1(3); 143-9). The clinically induced disease typically becomes manifest at approximately day 8-10 after inoculation. The symptoms that are observed in animals vary from mild gait disturbances and tail atony to complete paralysis and death. These clinical manifestations are given a clinical score ranging from 0 to 5. In the present situation, the scores were based on the following criteria: clinical score 0, no signs; 1.0 limp tail; 2.0 limptail with loss of righting; 3.0 paralysis of single hind limb; 4.0 paralysis of both hind limbs; 5.0 death. Weight loss typically occurs. In animals that survive, spontaneous recovery occurs, accompanied by variable recovery of most motor function. Depending on the species, allergen, and methodology used, animals tested by the EAE model may experience a single (acute EAE) or several (chronic relapsing EAE) attacks.

Methodology

Experimental autoimmune encephalomyelitis was induced in C57BL/6 mice using the following protocol. Female C57BL/6 mice (6-8 weeks old, N=24) purchased from Jackson Labs, were allowed to acclimate for one week prior to EAE induction. EAE was induced using myelin oligodendrocyte glycoprotein peptide 35-55 ($MOG_{35-55}$, MEVGWYRSPFSRVVHL-YRNGK). The $MOG_{35-55}$ injection with Freund's adjuvant was administered subcutaneously adjacent to the hind leg. At the same time, the animals received an injection of pertussis toxin (200 ng in 200 μL phosphate buffered saline (PBS), intraperitoneally), and a second pertussis toxin injection two days later. Mice were given a booster injection of $MOG_{35-55}$ at day No. 7. Two or three days after the second MOG booster injection, some animals begin to show signs of EAE. The mice are monitored daily using the clinical scoring system described above.

Example 1

The data depicted in FIG. 1 indicate that the Didox treatment, indicated by the line having solid squares (■), reduced the severity and delayed the onset of the clinical manifestation of the disease. In addition, Didox delayed the onset of the disease in the minority of animals in which it occurred in the Didox treatment group, 7.3 days versus 4.4 days for the control group. As the data indicate, the severity of clinical manifestation of the disease was significantly reduced in the Didox treated group throughout the course of the experiment. For example, at the plateau of the clinical condition on day 12 for both the Didox and saline (control) group, represented by the open squares (☒), the mean clinical score was only 0.45 for the Didox treated cohort compared to a score of 1.9 for the control group. As seen in Table A herein below, treatment with Didox resulted in a decrease in the percentage of animals that exhibited any clinical symptom of the disease, 27% in the Didox treatment group in comparison to the control, wherein 78% of the mice exhibited clinical symptoms.

TABLE A

| Group | Incidence | Max. Score | Max. Score (mean +/− SEM) | Day of Disease Onset |
|---|---|---|---|---|
| Control | 7/9 (78%) | 3.5 | 1.9 +/− 0.39 | 4.43 +/− 1.23 |
| Didox | 3/11 (27%) | 3 | 0.45 +/− 0.31 | 7.33 +/− 1.73 |

Example 2

Experimental autoimmune encephalomyelitis was induced in C57BL/6 mice using the following protocol. Female C57BL/6 mice (6-8 weeks old, N=16) purchased from Jackson Labs, were allowed to acclimate for one week prior to EAE induction. EAE was induced using myelin oligodendrocyte glycoprotein peptide 35-55 ($MOG_{35-55}$, MEVGWYRSPFSRVVHL-YRNGK). The $MOG_{35-55}$ injection with Freund's adjuvant was administered subcutaneously adjacent to the hind leg. At the same time, the animals received an injection of pertussis toxin (200 ng in 200 μL phosphate buffered saline (PBS), intraperitoneally), and a second pertussis toxin injection two days later. Mice were given a booster injection of $MOG_{35-55}$ at day No. 7.

Figure 2:
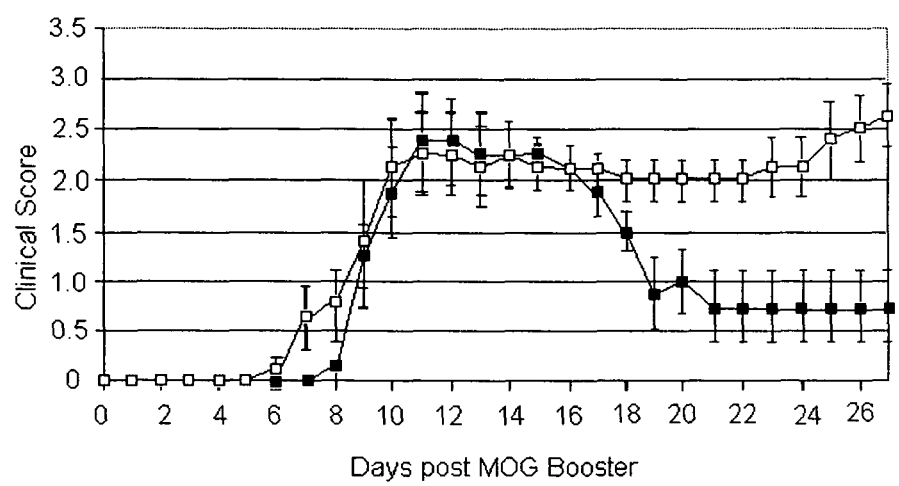
FIG. 2 depicts the ability of N,3,4-trihydroxybenzamide (Didox) to treat C57BL/6 mice from further developing neuromuscular symptoms and to reduce the already present clinical symptoms in animals that have been treated in order to induce experimental autoimmune encephalomyelitis (EAE). The line indicated with open squares (☒) represents the control group which are untreated after developing the symptoms of EAE. The line indicated with solid squares (■) represents animals treated with N,3,4-trihydroxybenzamide at day 16 after receiving a MOG booster according to Example 2.

The EAE was allowed to progress for 16 days after the $MOG_{35-55}$ booster. Clinical symptoms were well established at this point. After this time the animals were divided into two groups with matching clinical scores. The first group (N=11) was administered N,3,4-trihydroxybenzamide (Didox) (250 mg/kg) intraperitoneally. The second group (N=13) (control) was treated with 0.15 M NaCl. FIG. 2 is a graph of the results of this experiment. The first group represented by the line having solid squares (■) was able to show reduced signs of neuropathy whereas the untreated group represented by the line having the open squares (☒) continued to manifest signs of EAE. The Didox treatment group achieved a more than 50% reduction in average clinical score.

Example 3

Figure 3:
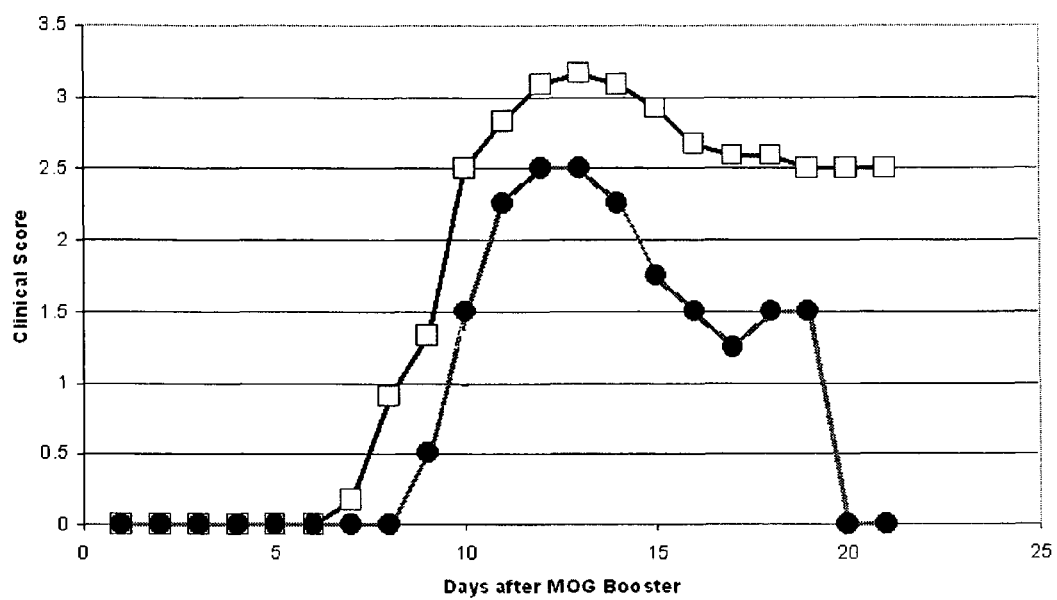
FIG. 3 depicts the ability of ethyl N',3,4,5-tetrahydroxybenzenecarboximidate to prophylactically protect C57BL/6 mice from developing neuromuscular symptoms when the animals have been treated to induce experimental autoimmune encephalomyelitis (EAE). The line indicated with open squares (☒) represents the control animals which manifest EAE symptoms 5-7 days post MOG booster and continue to develop symptoms. The line indicated with solid squares (✶) represents animals treated with ethyl N',3,4,5-tetrahydroxybenzenecarboximidate to two days prior to MOG booster (day-2) according to Example 3.

Similarly to Example 1, Female C57BL/6 mice were induced with EAE and divided into two groups. The controls were untreated while the other group was given ethyl N',3,4,5-trihydroxybenzenecarboximidate. FIG. 3 depicts the results of this experiment showing the ability of the disclosed ribonucleotide reductase inhibitors to treat neurodegenerative diseases. Animals treated with ethyl N',3,4,5-trihydroxybenzenecarboximidate manifested the symptoms indicated by the solid circle (★) line while the untreated animals (control) manifested the symptoms indicated by the open square (☒) line.

Example 4

Figure 4:
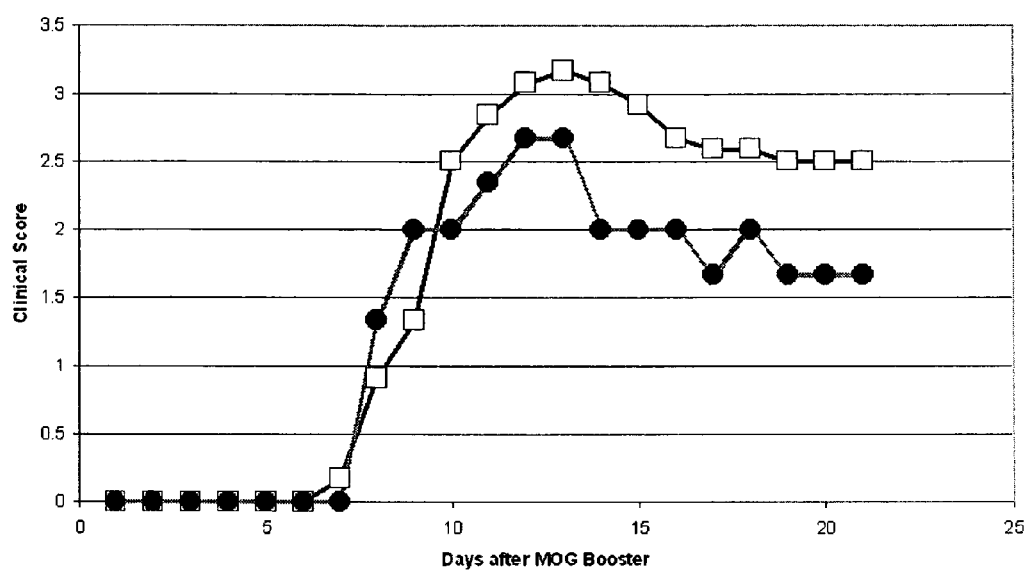
FIG. 4 depicts the ability of N',3,4,5-tetrahydroxybenzenecarboximidamide (Trimidox) to prophylactically protect C57BL/6 mice from developing neuromuscular symptoms when the animals have been treated to induce experimental autoimmune encephalomyelitis (EAE). The line indicated with open squares (☒) represents the control animals, which manifest EAE symptoms 5-7 days post MOG booster and continue to develop symptoms. The line indicated with solid squares (✶) represents animals treated with N',3,4,5-tetrahydroxybenzenecarboximidamide to two days prior to MOG booster (day-2) according to Example 4.

Similarly to Example 1, Female C57BL/6 mice were induced with EAE and divided into two groups. The controls were untreated while the other group was given N',3,4,5-tetrahydroxybenzenecarboximidamide (Trimidox). FIG. 4 depicts the results of this experiment showing the ability of the disclosed ribonucleotide reductase inhibitors to treat neurodegenerative diseases. Animals treated with ethyl N',3,4,5-trihydroxybenzenecarboximidate.HCl (Imidate) manifested the symptoms indicated by the solid circle (★) line while the untreated animals (control) manifested the symptoms indicated by the open square (☒) line.

Example 5

Figure 5:
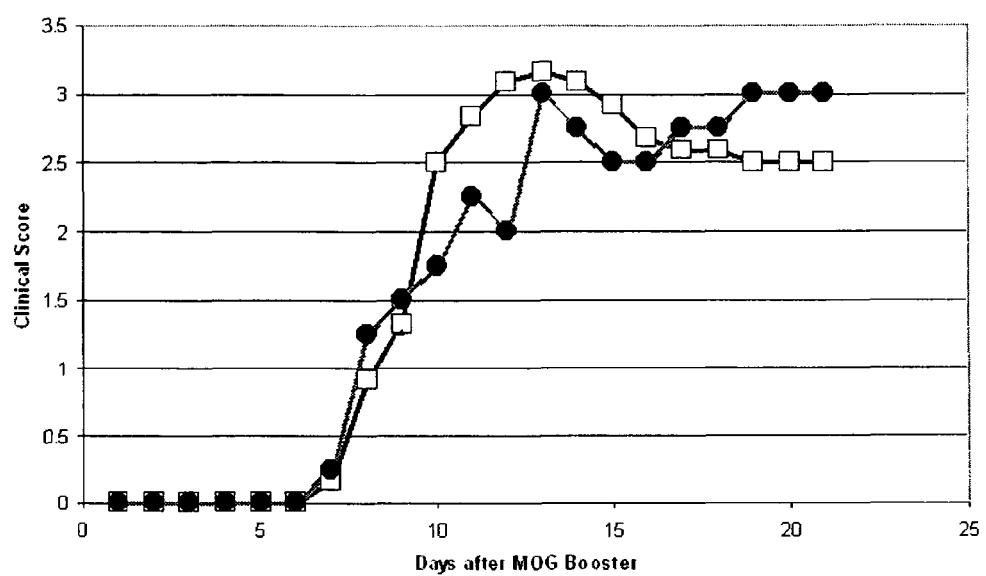
FIG. 5 depicts the ability of hydroxyurea to prophylactically protect C57BL/6 mice from developing neuromuscular symptoms when the animals have been treated to induce experimental autoimmune encephalomyelitis (EAE). The line indicated with open squares (✶) represents the control animals which manifest EAE symptoms 5-7 days post MOG booster and continue to develop symptoms. The line indicated with solid squares (⊠) represents animals treated with hydroxyurea to two days prior to MOG booster (day-2) according to Example 4.

Similarly to Example 1, Female C57BL/6 mice were induced with EAE and divided into two groups. The controls were untreated while other group was given hydroxyurea. FIG. 5 depicts the results of this experiment. The disclosed compound, hydroxyurea did not show evidence of treating neurodegenerative diseases. Animals treated with hydroxyurea manifested the symptoms indicated by the solid circle (★) line while the untreated animals (control) manifested the symptoms indicated by the open square (☒) line.

Example 6

The effect of Didox on cytokine levels was tested. As before, two groups were assembled, one treated with Didox while the other group served as a control and only received saline injections. The Didox treatment did not begin until the EAE mice had reached clinical stage 2 or more versus a similar group that was treated with saline. EAE was initiated in all animals depicted at the same time and in an identical manner. All animals were of the same experimental time point at the time of serum collection for cytokine analysis. The Didox treated group experienced a decrease of two points in the EAE clinical score. The analysis of cytokine levels was performed by utilizing a BioPlex® multiplexable bead assay method that simultaneously quantitates mouse cytokines in diverse matrices. In this example the assay was carried out on serum derived from mice of the two groups (Didox and saline treated) at day 12 post MOG induced EAE. Blood was obtained by cardiac aspiration from mice that had been euthanized by $CO_2$. Serum was obtained from clotted blood after centrifugation and stored at 800° C. until assayed. For analysis the serum was diluted and analyzed with the Bio-Plex® assay system. The system utilized beads that are internally labeled with two fluorescent dyes (one for identification of the bead and one for covalent attachment of ligands (or biomolecules). Once an antibody was conjugated to the bead a sample of serum was added and followed by a reporter antibody that is often biotinylated. Following incubation with biotinylated reporter antibody, strepavidin/phycoerythrin was added to make detection possible. The system can profile up to 23 mouse cytokines. Table B indicates the amount of cytokine present (pg/mL) in the serum.

TABLE B

| Cytokine | control | Didox | cytokine | control | Didox |
|---|---|---|---|---|---|
| IL-2 | 2 ± 2 | 0.7 ± 0.2 | IFN-g | 10 ± 3 | 3 ± 1 |
| IL-4 | 0 ± 0 | 0 ± 0 | TNF-α | 219 ± 132 | 61 ± 46 |
| IL-5 | 6 ± 5 | 2 ± 1 | IL-12 | 559 ± 276 | 36 ± 14 |
| IL-10 | 16 ± 7 | 3 ± 1 | IL-17 | 83 ± 29 | 2 ± 0.2 |
| GM-CSF | 7 ± 4 | 0.4 ± 0.5 | | | |

Figure 6:
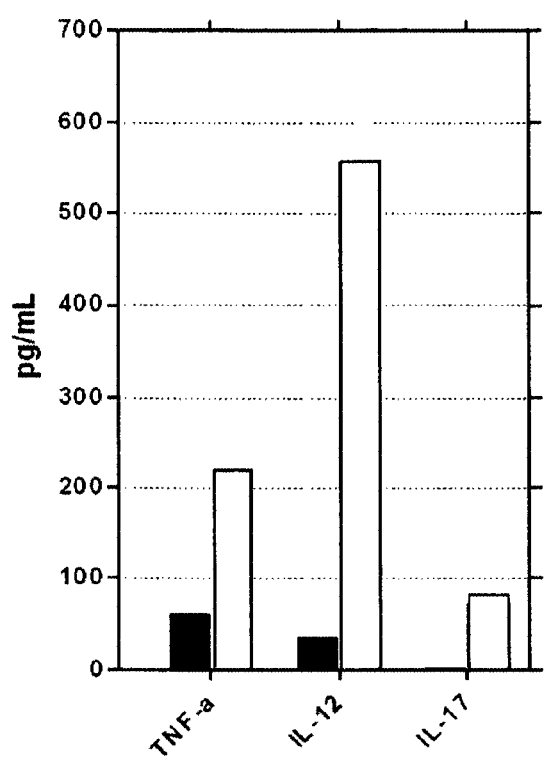
FIG. 6 depicts the reduction in the levels of the proinflammatory cytokines TNF-α, IL-10 and IL-12 in C57BL/6 mice treated with Didox (solid black bars) versus animals given only saline (solid white bars).

FIG. 6 depicts the reduction in the levels of the proinflammatory cytokines TNF-α, IL-10 and IL-12 in the serum from Didox-treated EAE mice compared to saline treated EAE mice. As reported in Table A and depicted in FIG. 6, the reduction in these inflammatory cytokines was 3.5 fold for TNF levels, 5.0 fold for Il-10 and 15 fold for IL-12.

The reduction in the $T_H$-3 ($T_H$-17/23) pathway marker IL-17 was approximately 35 fold. As such, because IL-17 has now been implicated in various models of immune-mediated tissue injury, including organ specific autoimmunity in the brain, heart, synovium and intestine, allergic disorder of lung and skin and microbial infection of the intestines and nervous system, administration of the disclosed compounds can be used to treat autoimmune disorders and stroke. For example, the pathway named $T_H$17 is now credited (Steinman, 2007 Nature Med. 13, 139-145.) for causing and sustaining tissue damage in these diverse medical situations. The medical conditions that aberrant levels of IL-17 have been best documented to be associated with are multiple sclerosis, rheumatoid arthritis, Crohn's disease, allergic conditions, pathogenesis of myocarditis, and ulcerative colitis, generally described as an autoimmune condition. The importance of IL-17 has also been recently shown in the pathogenesis of stroke. (Kostulas et al. 1999 Stroke 10:2174-2179).

Example 7

Figure 7:
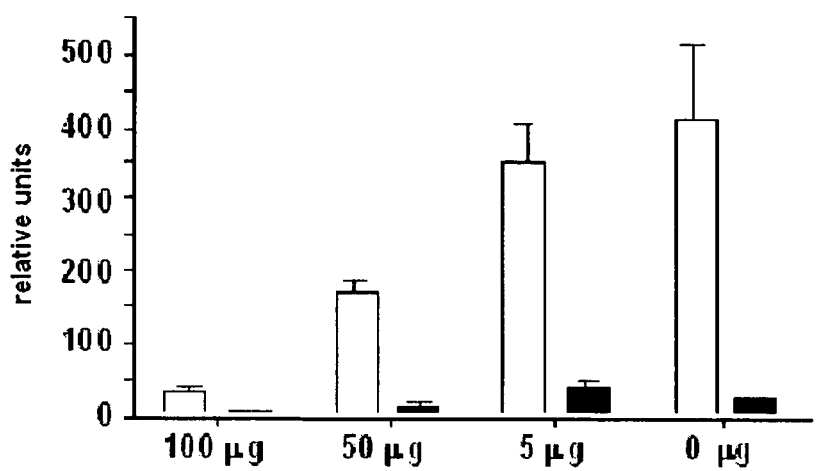
FIG. 7 depicts the effect of varying concentrations of Didox on T-Cell proliferation. Splenocytes were stimulated with CD3/CD28 and treated with Didox. This figure shows that the level of T-Cell proliferation is reduced to that for un-stimulated cells.

A series of in vitro experiments were conducted to ascertain the effect of Didox on immune function. A mixed splenocyte preparation was divided into two portions, one was stimulated with CD3 and CD28 to specifically activate T-cells while the other served as a control. The splenocytes were isolated from female C57BL/6 mice (6-8 weeks old) and the splenocytes were incubated for 24 hours with CD3/CD28 coated wells, after which Didox was added at varying concentrations. The cells were then incubated for an additional 48 hours. Each well was labeled with BrdU for the last 24 hours and the wells analyzed according to the manufacturer's instructions (Roche-Cell Proliferation Chemiluminescent assay kit). FIG. 7 depicts the results of these experiments. The solid black bars represent un-stimulated splenocytes while the white bars the effect of varying concentrations of Didox on the amount of T-Cells present. At a concentration of 100 μM, Didox reduces the level of T-cells to the amount present in un-stimulated cells.

Example 8

Figure 8:
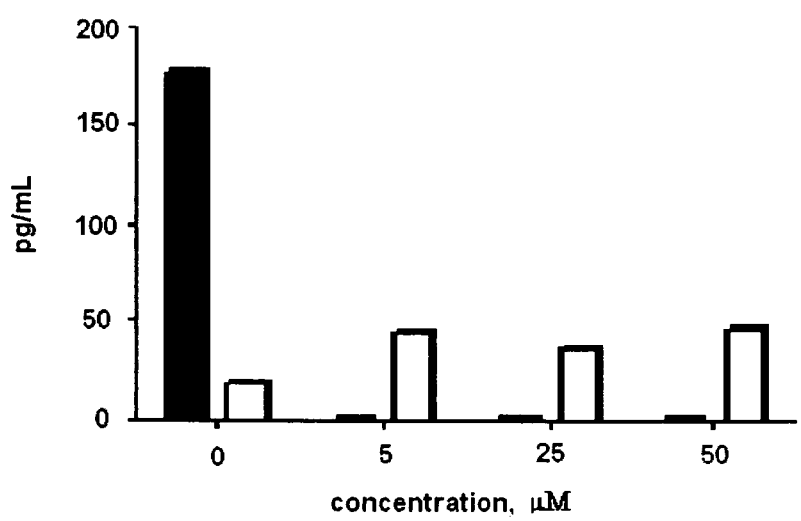
FIG. 8 depicts the effect of varying concentrations of Didox on the secretion of inflammatory cytokines by T-Cells. This figure shows that 48 hour treatment of activated T-Cells reduces the secretion of IL-17 down to baseline levels.
Figure 9:
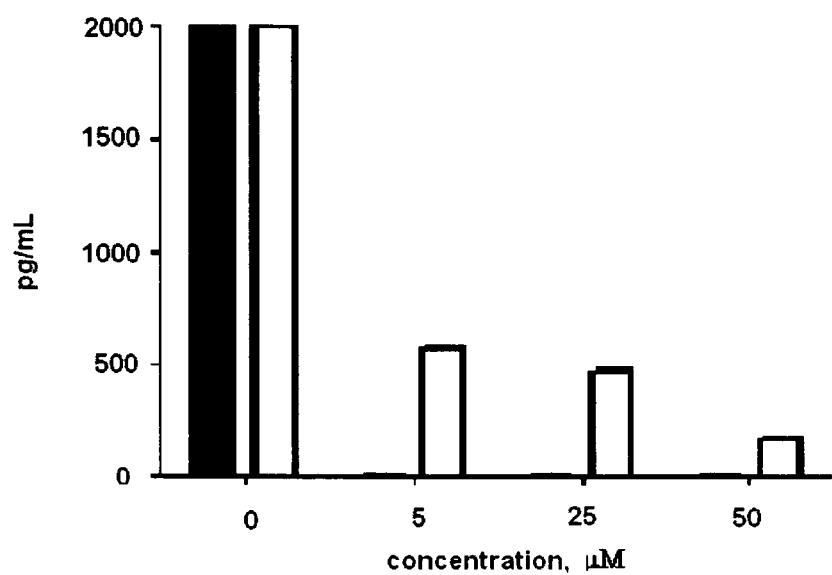
FIG. 9 depicts the effect of varying concentrations of Didox on the secretion of inflammatory cytokines by T-Cells. This figure shows that 48 hour treatment of activated T-Cells reduces the secretion of IFNγ down to baseline levels.

The purpose of this example was to determine whether Didox treatment of T-Cells in vitro produced similar data as was found in vivo using the EAE model. As shown in FIG. 8 and FIG. 9, Didox treatment for 48 hours reduces the secretion of the inflammatory cytokines IL-17 and IFNγ respectively down to baseline even at a Didox concentration of 5 μM. Shorter treatment time (24 hours) with Didox does not reduce the levels of these cytokines to background although the levels of IFNγ are reduced to less than half the level secreted by the untreated activated T-cells by 24 hours.

Example 9

Figure 10:
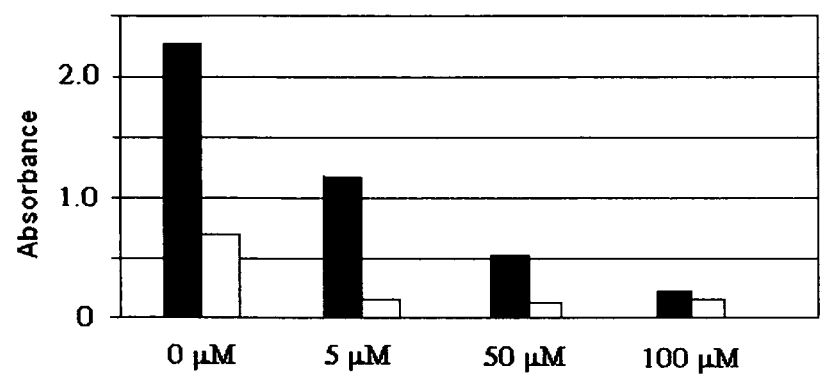
FIG. 10 depicts the effect of Didox on the production of nitrite by activated microglia. This figure shows a dose dependent attenuation of nitrite production in the presence of Didox.

To further evaluate the beneficial effect of Didox on brain tissue, we analyzed the ability of Didox to attenuate the production of nitrite by activated microglia, which are major contributors to the inflammatory status of EAE mice. Microglia were isolated from rat brain and activated with lipopolysaccharide (LPS) in the presence or absence of increasing concentrations of Didox. The results are shown in FIG. 10. We observed a dose dependent attenuation of nitrite production (solid bars) vs media (white bars), which reached base line levels with a 100 μM treatment. This observation, together with the attenuation of the T-cell inflammatory response would both contribute to the biological activity of Didox to reduce the severity of EAE.

Compositions

Disclosed herein are compositions that comprise one or more of the disclosed compounds, for example, a composition comprising:
a) an effective amount of one or more ribonucleotide reductase inhibitors as disclosed herein; and
b) a pharmaceutically acceptable carrier.
Further disclosed are compositions comprising:
a) an effective amount of one or more ribonucleotide reductase inhibitors as disclosed herein; and
b) a pharmaceutically acceptable carrier.
Also disclosed are compositions comprising:
a) an effective amount of one or more ribonucleotide reductase inhibitors as disclosed herein; and
b) a pharmaceutically acceptable carrier.
A further yet example is a composition comprising:
a) an effective amount of one or more ribonucleotide reductase inhibitors as disclosed herein;
b) one or more compounds effective as a treatment for neurodegenerative and/or autoimmune diseases; and
c) a pharmaceutically acceptable carrier.
One still further composition disclosed herein:
a) an effective amount of one or more ribonucleotide reductase inhibitors as disclosed herein;
b) one or more compounds chosen from interferon β1-a, interferon β1-b, interferon α, glatiramer acetate, methylprednisolone, prednisone, mitoxantrone, methotrexate, azathioprine, cladribine, cyclophosphamide, cyclosporine, tysabri; and
c) a pharmaceutically acceptable carrier.
Yet further disclosed herein are compositions comprising:
a) an effective amount of one or more ribonucleotide reductase inhibitors as disclosed herein;
b) one or more compounds chosen from interferon β1-a, interferon β1-b, interferon α, glatiramer acetate, methylprednisolone, prednisone, mitoxantrone, methotrexate, azathioprine, cladribine, cyclophosphamide, cyclosporine, tysabri;
c) one or more compounds chosen from FTY-720 (fingolimod), MBP8298 (dirucotide), liquinimod, 4-aminopyridine (4AP), lovastatin, and pravastatin; and
d) a pharmaceutically acceptable carrier.

As described herein above, the formulations of the present disclosure include pharmaceutical compositions comprising one or more of the disclosed ribonucleotide reductase inhibitors that can inhibit the activity of ribonucleotide reductase and therefore is suitable for use in preventing or treating a neuroinflammatory or autoimmune disease and a pharmaceutically-acceptable carrier, vehicle, or diluent. Those skilled in the art based upon the present description and the nature of any given inhibitor identified by the assays of the present invention will understand how to determine a therapeutically effective dose thereof.

The pharmaceutical compositions may be manufactured using any suitable means, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically or pharmaceutically acceptable carriers (vehicles, or diluents) comprising excipients and auxiliaries which facilitate processing of the active disclosed ribonucleotide reductase inhibitors into preparations which can be used pharmaceutically. Proper formulation is dependent upon the route of administration chosen.

Any suitable method of administering a pharmaceutical composition to a patient may be used in the methods of treatment of the present invention, including injection, transmucosal, oral, inhalation, ocular, rectal, long acting implantation, liposomes, emulsion, or sustained release means.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. For ocular administration, suspensions in an appropriate saline solution are used as is well known in the art.

For oral administration, the disclosed ribonucleotide reductase inhibitors can be formulated readily by combining the active disclosed ribonucleotide reductase inhibitors with pharmaceutically acceptable carriers well known in the art. Such carriers enable the disclosed ribonucleotide reductase inhibitors of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active disclosed ribonucleotide reductase inhibitors may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the disclosed ribonucleotide reductase inhibitors for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The disclosed ribonucleotide reductase inhibitors may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active disclosed ribonucleotide reductase inhibitors in water-soluble form. Additionally, suspensions of the active disclosed ribonucleotide reductase inhibitors may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the disclosed ribonucleotide reductase inhibitors to allow for the preparation of highly concentrated solutions.

Alternatively, the active ingredient may be in powder form for constitution with a suitable vehicle, such as sterile pyrogen-free water, before use.

The disclosed ribonucleotide reductase inhibitors may also be formulated in rectal compositions such as suppositories or retention enemas, e.g., containing conventional suppository bases such as cocoa butter or other glycerides.

In addition to the formulations described previously, the disclosed ribonucleotide reductase inhibitors may also be formulated as a depot preparation. Such long acting formulations may be administered by implantation (for example subcutaneously or intramuscularly) or by intramuscular injection. Thus, for example, the disclosed ribonucleotide reductase inhibitors may be formulated with suitable polymeric or hydrophobic materials (for example as an emulsion in an acceptable oil) or ion exchange resins, or as sparingly soluble derivatives, for example, as a sparingly soluble salt.

One type of pharmaceutical carrier for hydrophobic disclosed ribonucleotide reductase inhibitors of the invention is a cosolvent system comprising benzyl alcohol, a nonpolar surfactant, a water-miscible organic polymer, and an aqueous phase.

The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic disclosed ribonucleotide reductase inhibitors well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical disclosed ribonucleotide reductase inhibitors may be employed. Liposomes and emulsions are well known examples of delivery vehicles or carriers for hydrophobic drugs. Certain organic solvents such as dimethylsulfoxide also may be employed.

Additionally, the disclosed ribonucleotide reductase inhibitors may be delivered using any suitable sustained-release system, such as semipermeable matrices of solid hydrophobic polymers containing the therapeutic agent. Various sustained-release materials have been established and are well known by those skilled in the art. Sustained-release capsules may, depending on their chemical nature, release the disclosed ribonucleotide reductase inhibitors for a prolonged period of time. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the agents of the invention may be provided as salts with pharmaceutically acceptable counterions. Salts tend to be more soluble in aqueous or other protonic solvents than are the corresponding free base forms.

Other aspects of the present invention include methods of treating a condition or a disease in a mammal comprising administering to said mammal a pharmaceutical composition of the present invention.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method of treating multiple sclerosis comprising administering a compound selected from the group consisting of:

i)

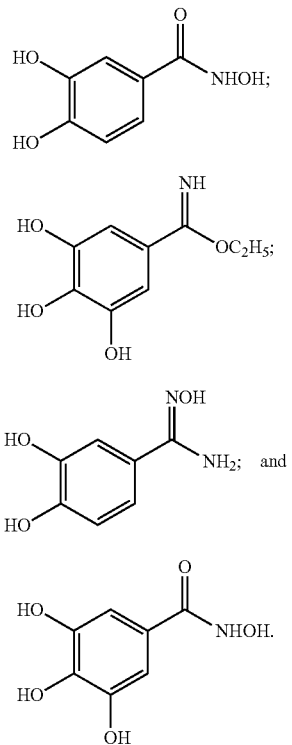

2. The method of claim 1, wherein the compound is

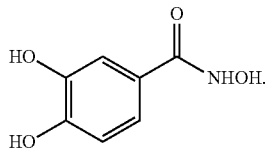

3. The method of claim 1, wherein the compound is

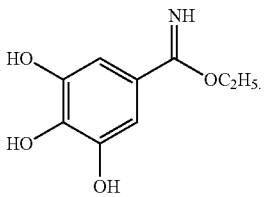 [SMILES: CCOC(=N)c1cc(O)c(O)c(O)c1]

4. The method of claim 1, wherein the compound is

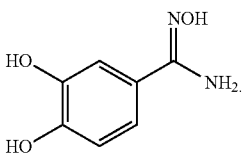

5. The method of claim 1, wherein the compound is

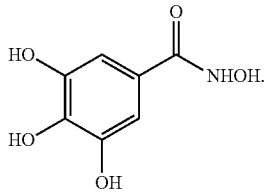

6. The method according to claim 1, further comprising administering one or more compounds selected from the group consisting of glatiramer acetate, mitoxantrone, tysabri, interferon β1-a, interferon β1-b, interferon α, methylprednisolone, prednisone, cyclophosphamide, methotrexate, azathioprine, cladribine, cyclosporine, FTY-720 (fingolimod), MBP8298 (dirucotide), liquinimod, 4-aminopyridine (4AP), lovastatin, and pravastatin.

* * * * *